(12) United States Patent
Brady et al.

(10) Patent No.: US 11,051,841 B2
(45) Date of Patent: Jul. 6, 2021

(54) MECHANICAL LOCKOUT FOR ULTRASONIC SURGICAL INSTRUMENT

(71) Applicant: ETHICON LLC, Guaynabo, PR (US)

(72) Inventors: John E. Brady, Liberty Township, OH (US); Alexander R. Cuti, Cincinnati, OH (US); Kevin M. Fiebig, Cincinnati, OH (US); Ellen Burkart, Cincinnati, OH (US); Demetrius N. Harris, Cincinnati, OH (US); Andrew Kolpitcke, Centerville, OH (US); Amy M. Krumm, Cincinnati, OH (US); Matthew T. Kuhn, Houston, TX (US); Jason R. Lesko, Cincinnati, OH (US); Stephen M. Leuck, Milford, OH (US); Guion Y. Lucas, Cincinnati, OH (US); Andrew S. Meyers, Cincinnati, OH (US); Candice Otrembiak, Loveland, OH (US); Grace E. Waters, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 243 days.

(21) Appl. No.: 15/951,788

(22) Filed: Apr. 12, 2018

(65) Prior Publication Data
US 2019/0314056 A1 Oct. 17, 2019

(51) Int. Cl.
*A61B 17/32* (2006.01)
*A61B 17/00* (2006.01)
(Continued)

(52) U.S. Cl.
CPC ............ *A61B 17/320092* (2013.01); *A61B 17/320068* (2013.01); *A61B 18/1445* (2013.01);
(Continued)

(58) Field of Classification Search
CPC .. A61B 2017/0046; A61B 2017/00464; A61B 17/320068; A61B 2090/0808; A61B 2090/0812; A61B 2017/320095
See application file for complete search history.

(56) References Cited

U.S. PATENT DOCUMENTS

| 5,322,055 | A | 6/1994 | Davison et al. |
| 5,873,873 | A | 2/1999 | Smith et al. |

(Continued)

FOREIGN PATENT DOCUMENTS

| EP | 1 199 040 A2 | 4/2002 |
| EP | 2 870 938 A1 | 5/2015 |

(Continued)

OTHER PUBLICATIONS

European Search Report, Extended, and Written Opinion dated Jul. 17, 2019 for Application No. 19168695.5, 8 pgs.
(Continued)

*Primary Examiner* — Majid Jamialahmadi
(74) *Attorney, Agent, or Firm* — Frost Brown Todd LLC

(57) ABSTRACT

An ultrasonic surgical instrument that includes a handle assembly including at least one user input feature; an ultrasonic transducer supported by the handle assembly, a shaft assembly configured to removably couple with the handle assembly, and a mechanical lockout assembly. The shaft assembly includes a distal end portion. The shaft assembly further includes an end effector extending distally from the distal end portion, and an ultrasonic waveguide configured to be acoustically coupled with the ultrasonic transducer. The mechanical lockout assembly is configured to move between at least an unlocked configuration and a locked configuration. In the locked configuration, the handle assembly and the shaft assembly are only partially coupled together physically preventing the user from activating the instrument using the user input feature. In the unlocked
(Continued)

configuration, the handle assembly and shaft assembly are completely coupled together enabling the user to activate the instrument using the user input feature.

15 Claims, 28 Drawing Sheets

(51) Int. Cl.
| | |
|---|---|
| *A61B 18/14* | (2006.01) |
| *A61B 17/29* | (2006.01) |
| *A61B 90/00* | (2016.01) |
| *A61B 18/00* | (2006.01) |

(52) U.S. Cl.
CPC ............... *A61B 2017/00402* (2013.01); *A61B 2017/00473* (2013.01); *A61B 2017/00477* (2013.01); *A61B 2017/320074* (2017.08); *A61B 2017/320095* (2017.08); *A61B 2018/00994* (2013.01)

(56) References Cited

U.S. PATENT DOCUMENTS

| | | | |
|---|---|---|---|
| 5,980,510 | A | 11/1999 | Tsonton et al. |
| 6,325,811 | B1 | 12/2001 | Messerly |
| 6,773,444 | B2 | 8/2004 | Messerly |
| 6,783,524 | B2 | 8/2004 | Anderson et al. |
| 8,663,220 | B2 | 3/2014 | Wiener et al. |
| 9,681,884 | B2 | 6/2017 | Clem et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0105750 | A1 | 4/2009 | Price et al. |
| 2010/0069940 | A1 | 3/2010 | Miller et al. |
| 2011/0015660 | A1 | 1/2011 | Wiener et al. |
| 2011/0087212 | A1 | 4/2011 | Aldridge et al. |
| 2012/0029546 | A1 | 2/2012 | Robertson |
| 2012/0112687 | A1 | 5/2012 | Houser et al. |
| 2012/0116265 | A1 | 5/2012 | Houser et al. |
| 2014/0005701 | A1 | 1/2014 | Olson et al. |
| 2014/0114334 | A1 | 4/2014 | Olson et al. |
| 2014/0330298 | A1 | 11/2014 | Arshonsky et al. |
| 2015/0080924 | A1 | 3/2015 | Stulen et al. |
| 2015/0080925 | A1 | 3/2015 | Schulte et al. |
| 2015/0141981 | A1 | 5/2015 | Price et al. |
| 2015/0148830 | A1* | 5/2015 | Stulen ............ A61B 17/320068 606/169 |
| 2017/0000541 | A1 | 1/2017 | Yates et al. |
| 2017/0105754 | A1 | 4/2017 | Boudreaux et al. |
| 2017/0105755 | A1 | 4/2017 | Boudreaux et al. |
| 2017/0105788 | A1 | 4/2017 | Boudreaux |
| 2018/0132926 | A1 | 5/2018 | Asher et al. |

FOREIGN PATENT DOCUMENTS

| | | |
|---|---|---|
| EP | 3 225 176 A1 | 10/2017 |
| WO | WO 2017/100412 A1 | 6/2017 |

OTHER PUBLICATIONS

European Search Report, Extended, and Written Opinion dated Jul. 5, 2019 for Application No. EP 19168712.8, 8 pgs.
European Search Report, Extended, and Written Opinion dated Jul. 3, 2019 for a No. EP 19168735.9, 8 pgs.
European Search Report, Extended, and Written Opinion dated Jul. 11, 2019 for Application No. EP 19168796.1, 8 pgs.
International Search Report and Written Opinion dated Jul. 3, 2019 for Application No. PCT/IB2019/053002, 15 pgs.
International Search Report and Written Opinion dated Jul. 11, 2019 for Application No. PCT/IB2019/053004, 12 pgs.
International Search Report and Written Opinion dated Jul. 11, 2019 for Application No. PCT/IB2019/053008, 12 pgs.
International Search Report and Written Opinion dated Jul. 17, 2019 for Application No. PCT/IB2019/053009, 11 pgs.
U.S. Appl. No. 61/410,603, entitled "Energy-Based Surgical Instruments," filed Nov. 5, 2010.
U.S. Appl. No. 62/363,411, entitled "Surgical Instrument with Dual Mode End Effector," filed Jul 18, 2016.
U.S. Appl. No. 15/644,930, entitled "Acoustic Drivetrain with External Collar at Nodal Position," filed Jul. 10, 2017.
U.S. Appl. No. 15/644,944, entitled "Features to Couple Acoustic Drivetrain Components in Ultrasonic Surgical Instrument," filed Jul. 10, 2017.
U.S. Appl. No. 15/951,747, entitled "Electrical Lockout for Ultrasonic Surgical Instrument," filed Apr. 12, 2018.
U.S. Appl. No. 15/951,773, entitled "Mechanical Lockout for Ultrasonic Surgical Instrument," filed Apr. 12, 2018.
U.S. Appl. No. 15/951,811, entitled "Mechanical Lockout for Ultrasonic Surgical Instrument," filed Apr. 12, 2018.
U.S. Appl. No. 15/951,747.
U.S. Appl. No. 15/951,773.
U.S. Appl. No. 15/951,811.

\* cited by examiner

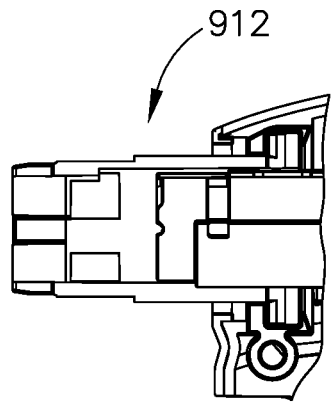
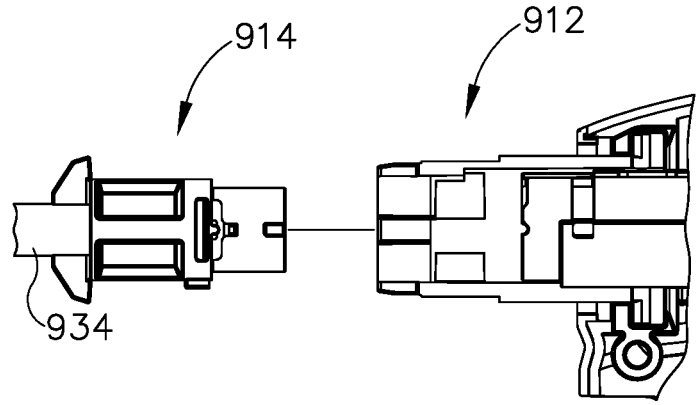
Fig.15A    Fig.15B
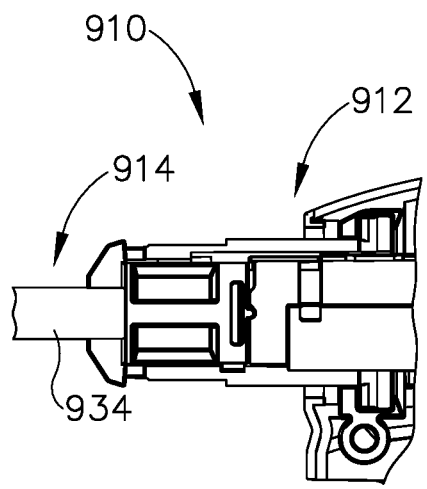
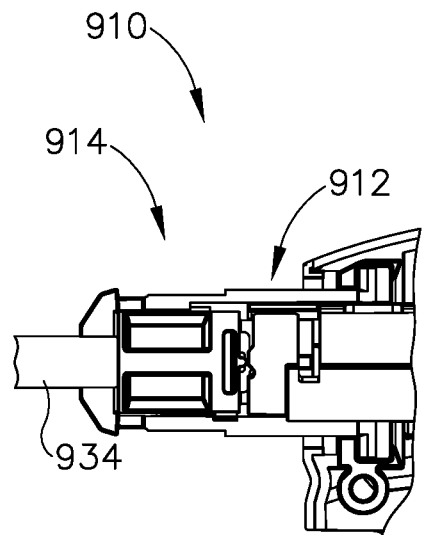
Fig.15C    Fig.15D

MECHANICAL LOCKOUT FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15A depicts a schematic side sectional view of an enlarged portion of the instrument similar to FIG. 14A in the unlocked configuration of FIG. 14A;

FIG. 15B depicts the schematic side sectional view of the enlarged portion of the instrument similar to FIG. 15A in the locked configuration of FIG. 14B as the shaft assembly is introduced;

FIG. 15C depicts the schematic side sectional view of the enlarged portion of the instrument similar to FIG. 15B, but in the locked configuration of FIG. 14C as the shaft assembly is inserted;

FIG. 15D depicts the schematic side sectional view of the enlarged portion of the instrument similar to FIG. 15C, but in the unlocked configuration of FIG. 14D;

Figure 1:
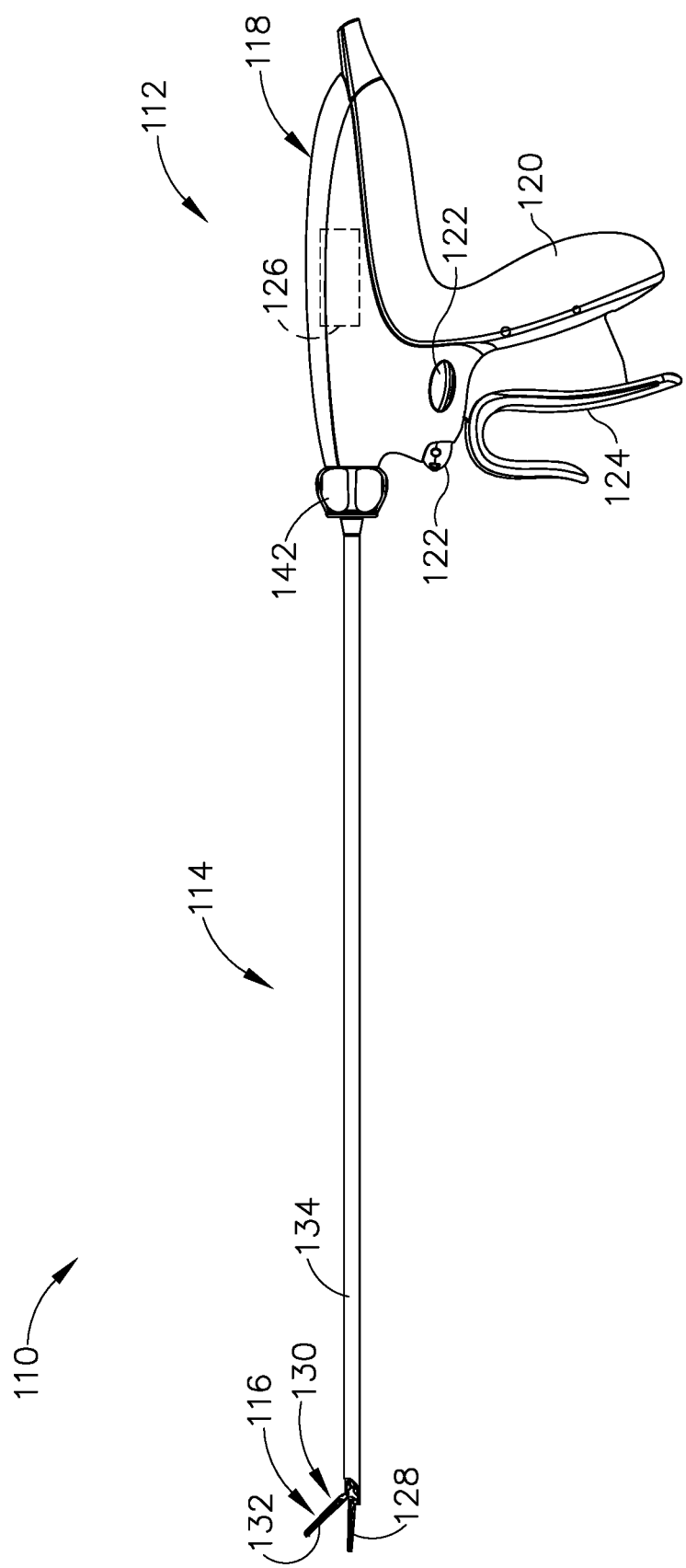
FIG. 1 depicts a side view of a first exemplary ultrasonic surgical instrument having a handle assembly and a shaft assembly with an end effector.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. FIRST EXEMPLARY ULTRASONIC SURGICAL INSTRUMENT FOR SURGICAL PROCEDURES

Figure 2A:
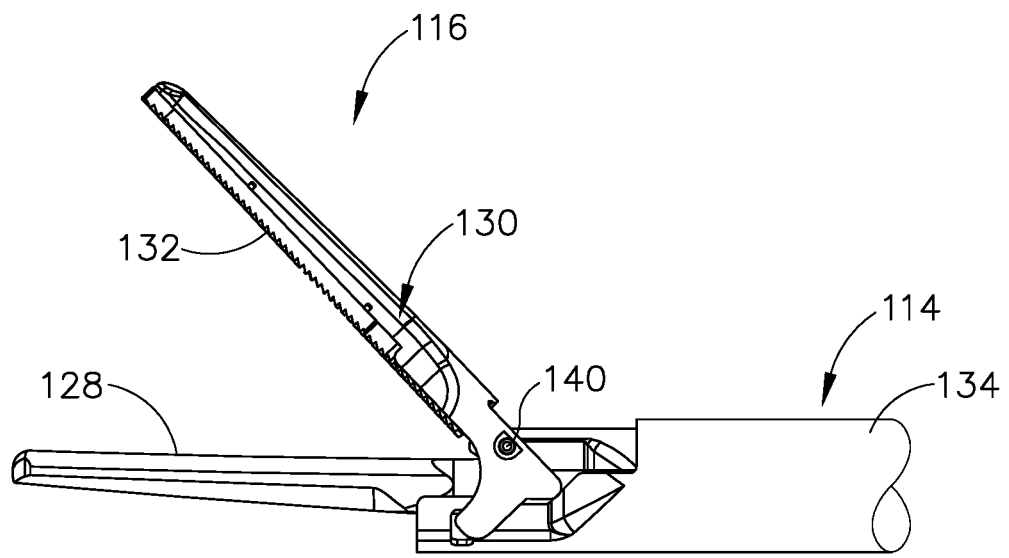
FIG. 2A depicts an enlarged side view of the end effector of FIG. 1 in an open configuration.
Figure 2B:
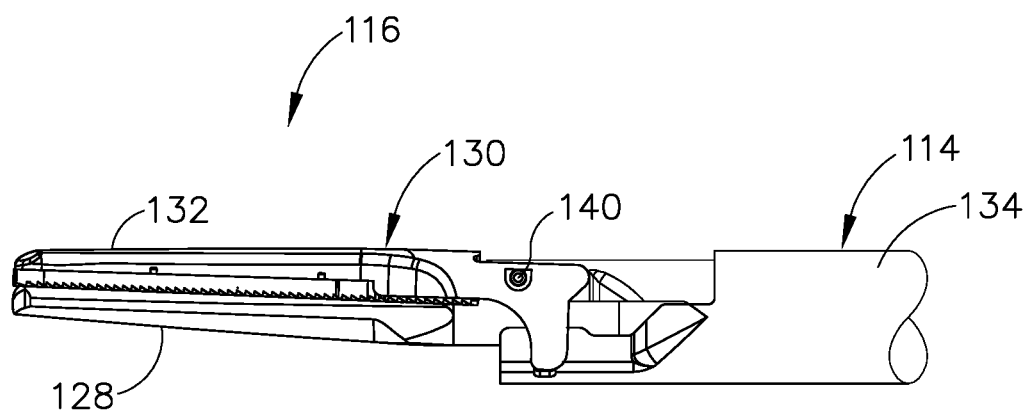
FIG. 2B depicts the enlarged side view of the end effector similar to FIG. 2A, but with the end effector in a closed configuration.

FIGS. 1-2B show a first exemplary ultrasonic surgical instrument (110) that includes a first modular assembly shown as a handle assembly (112), a second modular assembly shown as a shaft assembly (114) extending distally from handle assembly (112), and an end effector (116) arranged at a distal end of shaft assembly (114). Handle assembly (112) comprises a body (118) including a pistol grip (120) and energy control buttons (122) configured to be manipulated by a surgeon to control various aspects of tissue treatment energy delivered by surgical instrument (110). A trigger (124) is coupled to a lower portion of body (118) and is pivotable toward and away from pistol grip (120) to selectively actuate end effector (116). In other suitable variations of surgical instrument (110), handle assembly (112) may comprise a scissor grip configuration, for example. Body (118) houses an ultrasonic transducer (126), shown schematically in FIG. 1, configured to deliver ultrasonic energy to end effector (116), as described in greater detail below. Body (118) may also be referred to herein as a housing (118) and may include one component or an assembly of components. The terms "body" and "housing" are thus not intended to unnecessarily limit the invention described herein to any number of discrete components.

As shown best in FIGS. 2A-2B, end effector (116) includes an ultrasonic blade (128) and a clamp arm (130) configured to selectively pivot toward and away from ultrasonic blade (128) for clamping tissue therebetween. Clamp arm (130) includes a clamp pad (132) arranged on a clamping side thereof and is moveable from an open position shown in FIG. 2A to a closed position shown in FIG. 2B. With respect to FIG. 1, ultrasonic blade (128) is acoustically coupled with ultrasonic transducer (126), which is configured to drive (i.e., vibrate) ultrasonic blade (128) at ultrasonic frequencies for cutting and/or sealing tissue positioned in contact with ultrasonic blade (128). Clamp arm (130) is operatively coupled with trigger (124) such that clamp arm (130) is configured to pivot toward ultrasonic blade (128), to the closed position, in response to pivoting of trigger (124) toward pistol grip (120). Further, clamp arm (130) is configured to pivot away from ultrasonic blade (128), to the open position in response to pivoting of trigger (124) away from pistol grip (120). Various suitable ways in which clamp arm (130) may be coupled with trigger (124) will be apparent to those of ordinary skill in the art in view of the teachings provided herein. In some versions, one or more resilient members may be incorporated to bias clamp arm (130) and/or trigger (124) toward the open position.

Shaft assembly (114) of the present example extends along a longitudinal axis and includes an outer tube (134), an inner tube (136) received within outer tube (134), and an ultrasonic waveguide (138) supported within and extending longitudinally through inner tube (136). Ultrasonic blade (128) is formed integrally with and extends distally from waveguide (138). A proximal end of clamp arm (130) is pivotally coupled to distal ends of outer and inner tubes (134, 136), enabling clamp arm (130) to pivot relative to shaft assembly (114) about a pivot axis defined by a pivot pin (140) (see FIGS. 2A-2B) extending transversely through the distal end of inner tube (136).

In the present example, inner tube (136) is longitudinally fixed relative to handle assembly (118), and outer tube (134) is configured to translate relative to inner tube (136) and handle assembly (118), along the longitudinal axis of shaft assembly (114). As outer tube (134) translates distally, clamp arm (130) pivots about its pivot axis toward its open position. As outer tube (134) translates proximally, clamp arm (130) pivots about its pivot axis in an opposite direction toward its closed position. Though not shown, a proximal end of outer tube (134) is operatively coupled with trigger (124) such that actuation of trigger (124) causes translation of outer tube (134) relative to inner tube (136), thereby opening or closing clamp arm (130) as discussed above. In other suitable configurations not shown herein, outer tube (134) may be longitudinally fixed and inner tube (136) may be configured to translate for moving clamp arm (130) between the open and closed positions. Various other suitable mechanisms for actuating clamp arm (130) between the open and closed positions will be apparent to those of ordinary skill in the art.

Figure 3:
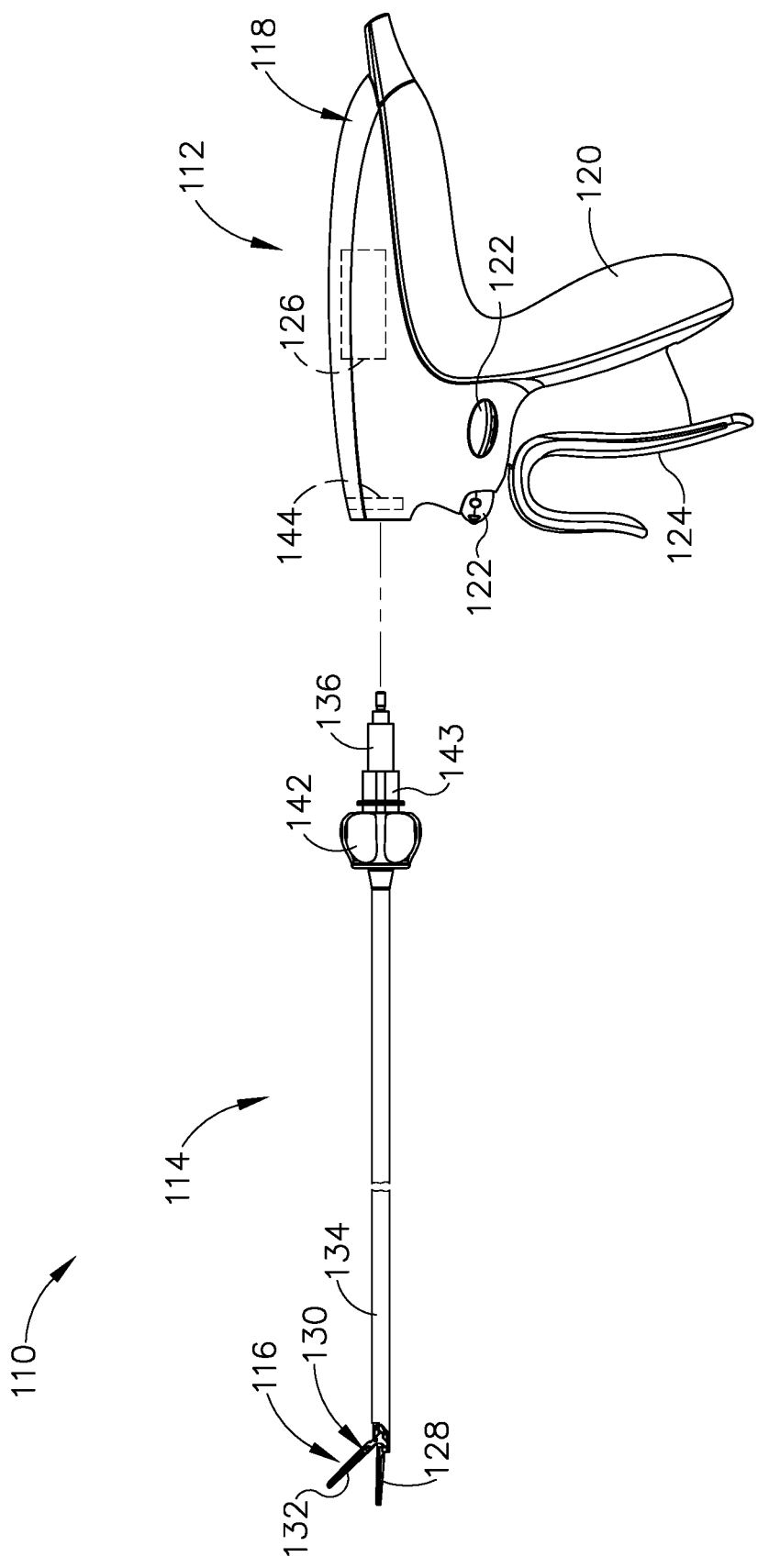
FIG. 3 depicts a partially exploded side view of the ultrasonic surgical instrument of FIG. 1.
Figure 4:
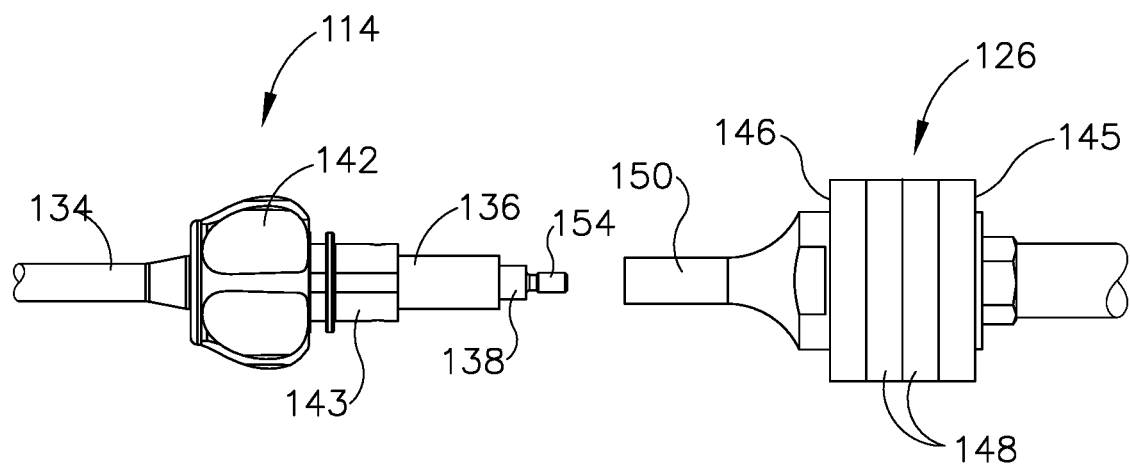
FIG. 4 depicts a partially schematic enlarged side view of an ultrasonic transducer, a waveguide, and a rotation knob of the ultrasonic surgical instrument of FIG. 1, showing attachment of the waveguide to the ultrasonic transducer.

Shaft assembly (114) and end effector (116) are configured to rotate together relative to body (118) about the longitudinal axis defined by shaft assembly (114). As shown in FIGS. 3-4, shaft assembly (114) further includes a rotation knob (142) arranged at a proximal end thereof as well as a shaft coupler (143) configured to mechanically connect to body coupler (144) of handle assembly (112). Rotation knob (142) is rotatably coupled to body (118) of handle assembly (112) and is rotationally fixed to outer tube (134), inner tube (136), and waveguide (138) by a coupling pin (not shown) extending transversely therethrough. Coupling pin (not shown) is arranged at a longitudinal location corresponding to an acoustic node of waveguide (138). In other examples, rotation knob (142) may be rotationally fixed to the remaining components of shaft assembly (114) in various other manners. Rotation knob (142) is configured to be gripped by an operator to selectively manipulate the rotational orientation of shaft assembly (114) and end effector (116) relative to handle assembly (112). Various examples of acoustic and mechanical connections between shaft assembly (114) and handle assembly (112) are described in greater detail in U.S. patent application Ser. No. 15/644,930, entitled "Acoustic Drivetrain with External Collar at Nodal Position," filed on Jul. 10, 2017, issued as U.S. Pat. No. 10,813,662 on Oct. 27, 20202, and U.S. patent application Ser. No. 15/644,944, entitled "Features to Couple Acoustic Drivetrain Components in Ultrasonic Surgical Instrument," filed on Jul. 10, 2017, issued as U.S. Pat. No. 10,709,470 on Jul. 14, 2020, the disclosures of which are each incorporated by reference herein.

FIGS. 1-3 show additional details of ultrasonic transducer (126) and waveguide (138). In particular, ultrasonic transducer (126) and waveguide (138) are configured to threadedly couple together. Accordingly, waveguide (138) is configured to acoustically couple ultrasonic transducer (126) with ultrasonic blade (128), and thereby communicate ultrasonic mechanical vibrations from ultrasonic transducer (126) to blade (128). In this manner, ultrasonic transducer (126), waveguide (138), and ultrasonic blade (128) together define an acoustic assembly of ultrasonic surgical instrument (110). Ultrasonic transducer (126) is rotatably supported within body (118) of handle assembly (112) and is configured to rotate with shaft assembly (114), including waveguide (138), and end effector (116) about the longitudinal axis of shaft assembly (114).

Ultrasonic transducer (126) is electrically coupled with a generator (not shown), which may be provided externally of ultrasonic surgical instrument (110) or integrated within surgical instrument (110). During use, generator (not shown) powers ultrasonic transducer (126) to produce ultrasonic mechanical vibrations, which are communicated distally through waveguide (138) to ultrasonic blade (128). Ultrasonic blade (128) is caused to oscillate longitudinally in the range of approximately 10 to 500 microns peak-to-peak, for example, and in some instances in the range of approximately 20 to 200 microns, at a predetermined vibratory frequency $f_o$ of approximately 50 kHz, for example. Vibrating ultrasonic blade (128) may be positioned in direct contact with tissue, with or without assistive clamping force provided by clamp arm (130), to impart ultrasonic vibrational energy to the tissue and thereby cut and/or seal the tissue. For example, blade (128) may cut through tissue clamped between clamp arm (130) and a clamping side of blade (128), or blade (128) may cut through tissue positioned in contact with an oppositely disposed non-clamping side of blade (128) having an edge, for example during a "back-cutting" movement. In some versions, waveguide (138) may be configured to amplify the ultrasonic vibrations delivered to blade (128). Waveguide (138) may include various features operable to control the gain of the vibrations, and/or features suitable to tune waveguide (138) to a selected resonant frequency.

Figure 5:
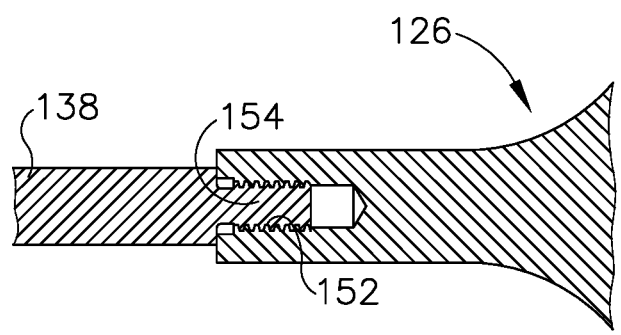
FIG. 5 depicts a partially schematic enlarged cross-sectional side view of a threaded coupling between the ultrasonic transducer and the waveguide of FIG. 4.

In the present example, ultrasonic transducer (26) includes a first resonator (or "end-bell") (145), a conically shaped second resonator (or "fore-bell") (146), and a transduction portion arranged between end-bell (145) and fore-bell (146) that includes a plurality of piezoelectric elements (148). A compression bolt (not shown) extends distally, coaxially through end-bell (145) and piezoelectric elements (148) and is threadedly received within a proximal end of fore-bell (146). A velocity transformer (or "horn") (150) extends distally from fore-bell (146) and includes an internally threaded bore (152) configured to receive and threadedly couple with an externally threaded proximal tip (154) of waveguide (38) as shown in FIGS. 4-5.

While the teachings herein are disclosed in connection with ultrasonic surgical instruments, it will be appreciated that they may also be employed in connection with surgical instruments configured to provide a combination of ultrasonic and radio frequency (RF) energies. Examples of such instruments and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

II. ALTERNATIVE EXEMPLARY ULTRASONIC SURGICAL INSTRUMENTS AND VARIOUS MECHANICAL LOCKOUT ASSEMBLIES

Given that various portions of ultrasonic surgical instrument (110) removably connect together, it may be desirable in various examples to reuse some portions of ultrasonic surgical instrument (110) while replacing others upon reconnection for further use by the surgeon. For example, the first modular assembly (12) in the present example is reusable whereas second modular assembly (114) may be disconnected and replaced with an unused, replacement second modular assembly (114). Since first modular assembly (112) is separable from second modular assembly (114), it is beneficial to ensure that first modular assembly (112) and second modular assembly (114) are correctly and completed assembled prior to use to prevent a malfunction or inadvertent separation of first modular assembly (112) from second modular assembly (114). For at least this reason, it may be desirable to incorporate a lockout assembly that prevents use of instrument (110) when the first modular assembly (112) and second modular assembly (114) are not correctly and completed assembled together.

While the following mechanical lockout assemblies (544, 544', 644, 744, 844, 944, 1044, 1144, 1244) are shown in distinct positions between reusable and replaceable features for removable connection, any of the following mechanical lockout assemblies (544, 544', 644, 744, 844, 944, 1044, 1144, 1244), it will be appreciated that mechanical lockout assemblies (544, 544', 644, 744, 844, 944, 1044, 1144, 1244) may be incorporated into any surgical instrument described herein, exchanged, or moved so as to make one or more portions of a surgical instrument removable from a remainder of the surgical instrument. Two general forms of mechanical lockout varieties are shown and described below. First, a mechanical lockout assembly that that effectively locks the clamp arm, thereby preventing the operator from clamping on tissue with the end effector. Second, a mechanical lockout assembly that effectively locks the energy control buttons, thereby preventing the operator from activating the ultrasonic blade. As such, mechanical lockout assemblies (544, 544', 644, 744, 844, 944, 1044, 1144, 1244) are intended to cover both energy control button lockouts preventing activation of ultrasonic blade and trigger lockouts preventing closure of clamp arm assembly toward ultrasonic blade. It is also appreciated that one or more of these mechanical lockout assemblies (544, 544', 644, 744, 844, 944, 1044, 1144, 1244) may be used in combination with another mechanical lockout assemblies (544, 544', 644, 744, 844, 944, 1044, 1144, 1244).

The following description provides various examples of mechanical lockout assemblies. Such mechanical lockout assemblies (544, 544', 644, 744, 844, 944, 1044, 1144, 1244) described below may be used with any ultrasonic surgical instrument described above and below and in any of the various procedures described in the various patent references cited herein. To this end, like numbers below indicate like features described above. Except as otherwise described below, ultrasonic surgical instruments (510, 610, 710, 810, 910, 1010, 1110, 1210) described below may be constructed and operable like instruments (110) described above. Certain details of ultrasonic surgical instruments (510, 610, 710, 810, 910, 1010, 1110, 1210) will therefore be omitted from the following description, it being understood that such details are already provided above in the description of instruments (110). Other suitable ways in which various ultrasonic surgical instruments may be used will be apparent to those of ordinary skill in the art in view of the teachings herein.

Similarly, various electrical lockouts may be incorporated into any surgical instrument in conjunction with the following mechanical lockouts (544, 544', 644, 744, 844, 944, 1044, 1144, 1244). Such electrical lockouts are disclosed in U.S. application Ser. No. 15/951,747, entitled "Electrical Lockout for Ultrasonic Surgical Instrument," filed on Apr. 12, 2018, published as U.S. Pub. No. 2019/0314054 on Oct. 17, 2019, the disclosure of which is incorporated by reference herein. Other suitable ways in which various ultrasonic surgical instruments may be used will be apparent to those of ordinary skill in the art in view of the teachings herein.

A. SECOND EXEMPLARY ULTRASONIC SURGICAL INSTRUMENT HAVING A FIRST EXAMPLE OF A MECHANICAL LOCKOUT ASSEMBLY

Figure 6:
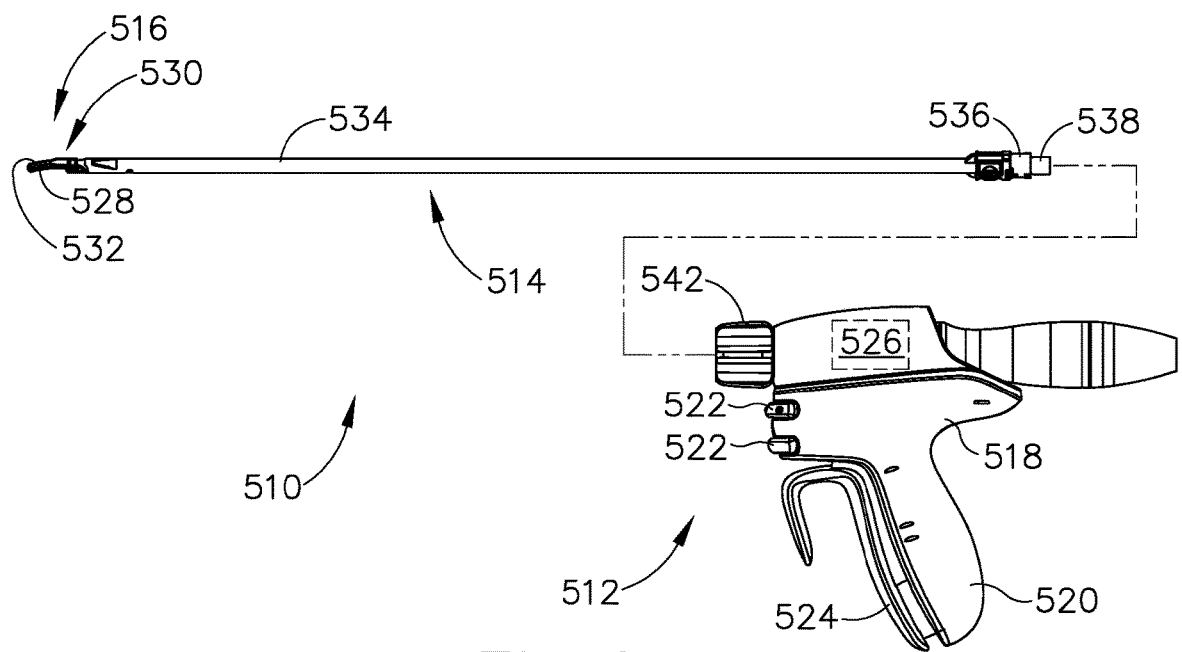
FIG. 6 depicts a schematic side view of a second exemplary ultrasonic surgical instrument.
Figures 7A, 7B:
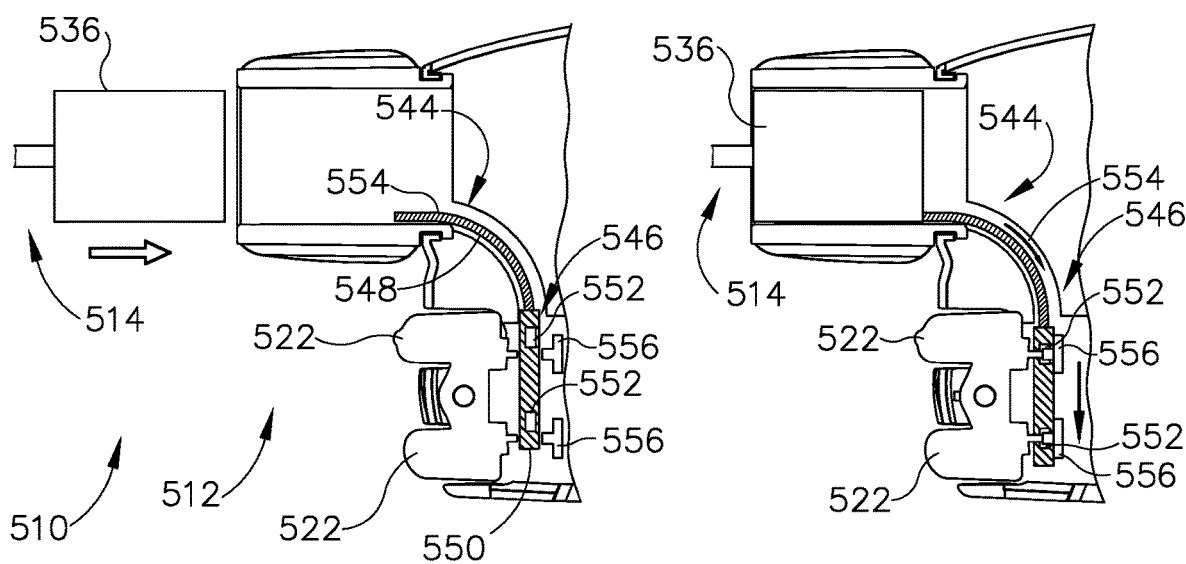
FIG. 7A depicts a schematic side sectional view of the instrument similar to FIG. 6 including a first exemplary mechanical lockout assembly in a locked configuration.
FIG. 7B depicts the schematic side sectional view of the instrument similar to FIG. 6, but in an unlocked configuration.

FIGS. 6-7B show a second exemplary ultrasonic surgical instrument (510) including a first mechanical lockout assembly (544). FIG. 6 shows ultrasonic surgical instrument (510) as comprising a first modular assembly shown as a handle assembly (512), a second modular assembly shown as a shaft assembly (514), an end effector (516), a body (518), a pistol grip (520), energy control buttons (522), a trigger (524), an ultrasonic transducer (526), an ultrasonic blade (528), a clamp arm (530), a clamp pad (532), an outer tube (534), an inner tube (536), an ultrasonic waveguide (538), and a rotation knob (542).

FIGS. 7A-7B show instrument (510) as including a mechanical lockout assembly (544). Mechanical lockout assembly (544) includes a barrier (546) that translates between a locked configuration and an unlocked configuration. Barrier (546) includes at least one body portion, with two body portions (548, 550) being shown in FIGS. 7A-7B. Body portion (550) includes at least one aperture (552) disposed within body portion (550), with two apertures (552) being shown in FIGS. 7A-7B. Barrier (546) is shown as a resilient elongated member that is disposed within handle assembly (512), however, barrier (546) may be operatively coupled to shaft assembly (514) and may be a variety of shapes and forms. Barrier (546) is laterally flexible and has sufficient column strength to drive body portion (550) without buckling. Handle assembly (512) includes energy control buttons (522) separated by a passageway (554) from switches (556). As shown in FIG. 7A, it is appreciated that aperture (550) may not extend completely through body portion (550) to enable energy control buttons (522) to mechanically actuate switches (556). As previously described with connection to the previous embodiment, while two energy control buttons (522) and two switches (556) are shown, more or fewer energy control buttons (522) and switches (556) are envisioned, for example, one or three. While not shown, the number of energy control button (534) and switches (556) may not be the same in some variations.

FIG. 7A shows instrument (510) in the locked configuration, where body portion (548) contacts and translates body portion (550) that is disposed between energy control buttons (522) and switches (556), preventing buttons (522) from activating switches (556), thereby preventing switches (556) from activating instrument (510). In moving to the unlocked configuration, barrier (546) is pushed by body portion (548) and translates into passageway (554) that extends between energy control buttons (522) and switches (556). In other words, the proximal portion of the shaft (514) pushes body portion (548), causing barrier (546) to translate into passageway (554) that extends between energy control buttons (522) and switches (556). As shown, engagement of shaft assembly (514) with handle assembly (512) pushes barrier (546) into a position that places apertures (550) in barrier (546) between energy control buttons (522) and switches (556).

FIG. 7B shows instrument (510) in the unlocked configuration, where apertures (552) are disposed between energy control buttons (522) and switches (556), enabling buttons (522) to activate switches (556), thereby enabling switches (556) to activate instrument (510). FIG. 7B shows where at least one of energy control button (522) or switch (556) extends at least partially within aperture (550) and contacts the other of energy control buttons (522) or switches (556) through aperture (550). FIG. 7B shows that the entire barrier (546) translates in passageway (554) towards energy control buttons (522) and switches (556). A spring (not shown), similar to spring (664) shown in FIGS. 9A-9B or spring (764) shown in FIGS. 11A-11B, or another suitable mechanism may be located at the bottom of barrier (546) to return barrier (546) to the locked configuration when shaft assembly (514) is removed from handle assembly (512).

B. SECOND EXEMPLARY ULTRASONIC SURGICAL INSTRUMENT HAVING A SECOND EXAMPLE OF A MECHANICAL LOCKOUT ASSEMBLY

Figure 8A:
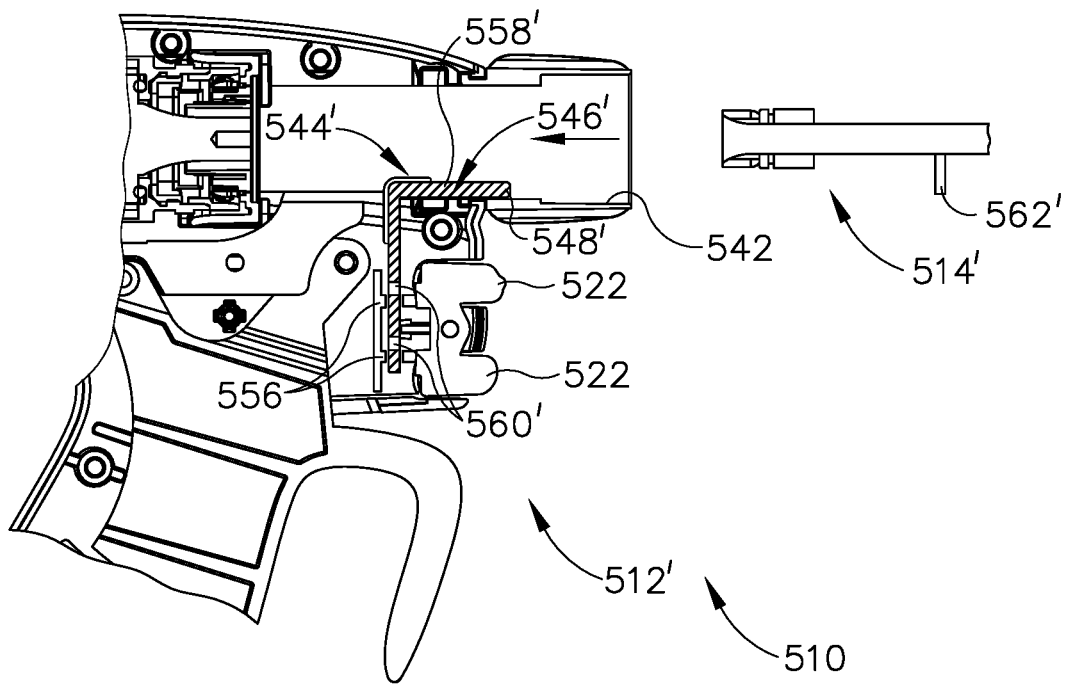
FIG. 8A depicts a schematic side sectional view of the instrument similar to FIG. 7A including a second exemplary mechanical lockout assembly in a locked configuration.
Figure 8B:
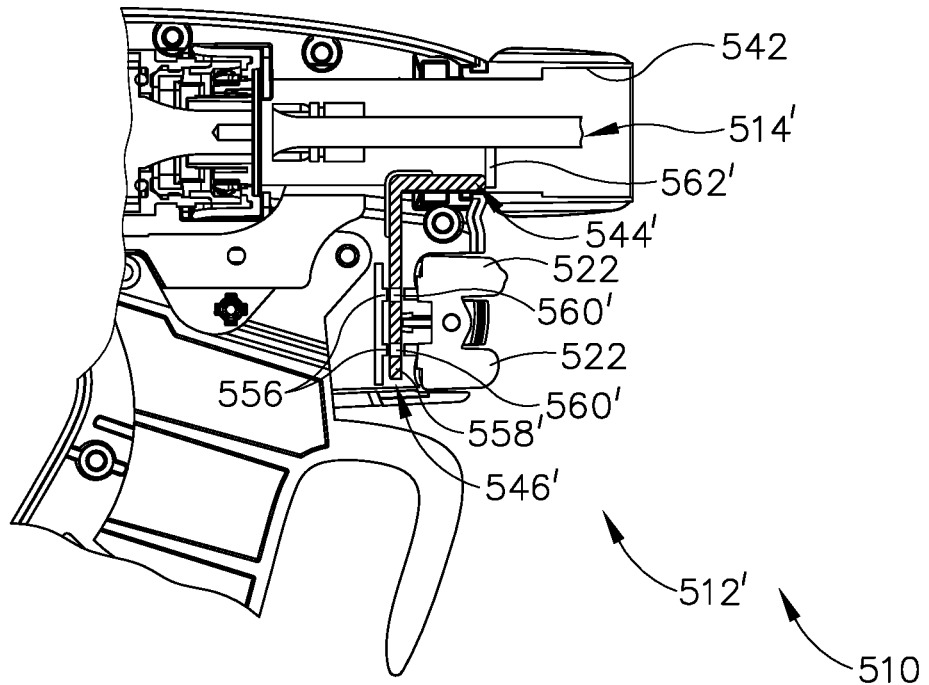
FIG. 8B depicts the schematic side sectional view of the instrument similar to FIG. 7B, but in an unlocked configuration.

FIGS. 8A-8B show another exemplary embodiment of a second mechanical lockout assembly (544'), where barrier (546') includes a single body portion (558') that includes apertures (560'). Additionally, apertures (560') extend completely through body portion (558') of barrier (546') in a generally perpendicular direction. Shaft assembly (514') includes a projection (562') that contacts barrier (546'), causing barrier (546') to translate, resulting in instrument (510) transitioning to the unlocked configuration, when shaft assembly (514') is fully coupled with handle assembly (512').

C. THIRD EXEMPLARY SURGICAL INSTRUMENT HAVING A THIRD EXAMPLE OF A MECHANICAL LOCKOUT ASSEMBLY

Figure 9A:
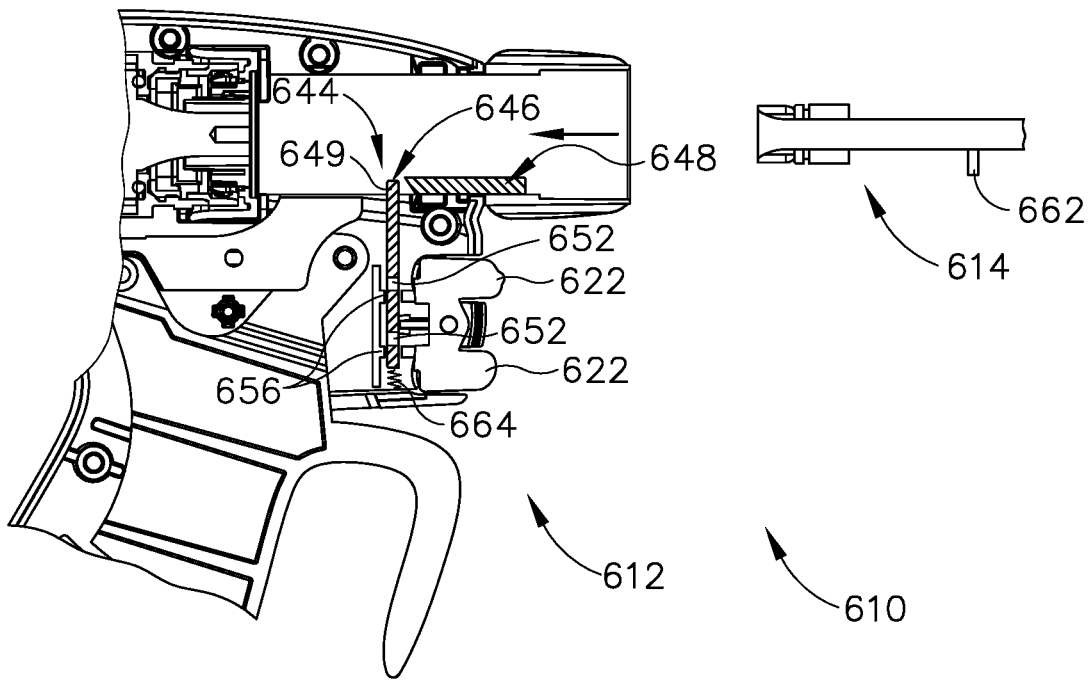
FIG. 9A depicts a schematic side view of a third exemplary ultrasonic surgical instrument including a third exemplary mechanical lockout assembly in a locked configuration.
Figure 9B:
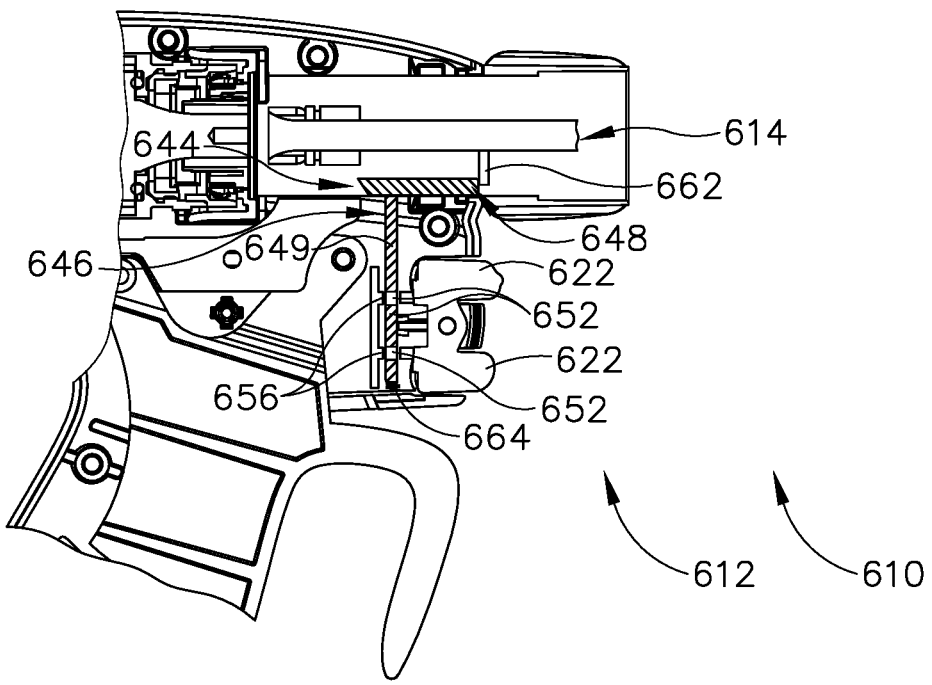
FIG. 9B depicts the schematic side view of the instrument similar to FIG. 9A, but in an unlocked configuration.

FIGS. 9A-9B show a third exemplary ultrasonic surgical instrument (610) including a third mechanical lockout assembly (644). Instrument (610) depicted in FIGS. 9A-9B is similar to instrument (510) depicted in FIGS. 8A-8B, with differences being briefly described below, and similarities being omitted. For example, instrument (610) includes a mechanical lockout assembly (644) that is different than mechanical lockout assembly (544) of instrument (510).

FIG. 9A shows instrument (610) in the locked configuration, where a first modular assembly is shown as a handle assembly (612) and a second modular assembly is shown as a shaft assembly (614) that are not completely coupled together. As a result, the operator is physically prevented from activating instrument (610) using energy control button (622) due to mechanical lockout assembly (644). As shown, mechanical lockout assembly (644) includes a barrier (646) such as a button lockout plate, and an angled slide (648), shaped as a wedge. Barrier (646) includes a body portion (649) and at least one aperture (652), with two apertures (652) being shown in FIG. 9A. In the locked configuration shown in FIG. 9A, barrier (646) is positioned such that apertures (652) are not interposed between buttons (622) and corresponding switches (656). Barrier (646) thus prevents buttons (622) from activating corresponding switches (656), thereby preventing activation of instrument (610).

Angled slide (648) of mechanical lockout assembly (644) is configured to be contacted by a projection (662) of shaft assembly (614) as shaft assembly (614) is coupled with handle assembly (612). As a result of being contacted by projection (662), angled slide (648) translates proximally and subsequently contacts barrier (646). The angled proximal end of slide (648) drives barrier (646) downwardly through a camming action. With barrier (646) in a downward position, apertures (652) are positioned between buttons (622) and corresponding switches (656), thereby providing clearance for buttons (622) to activate corresponding switches (656). Full coupling of shaft assembly (614) with handle assembly (612) thus causes instrument (610) to move from the locked configuration to the unlocked configuration.

FIG. 9B shows instrument (610) in the unlocked configuration, where handle assembly (612) and shaft assembly (614) are completely coupled together and the operator is able to activate instrument (610) using energy control button (622). Upon removal of shaft assembly (614), a resilient member, shown as a compression spring (664), causes barrier (646) to return to the locked configuration, where actuation of energy control buttons (622) is blocked from activating switches (656) by body portion (649) of barrier (646). Switches (656) may include button dome switches and corresponding printed circuit boards ("PCBs"). In the unlocked configuration, compression spring (664) is in a compressed state, whereas in the locked configuration (shown in FIG. 9A), compression spring (664) is in an extended state.

D. FOURTH EXEMPLARY ULTRASONIC SURGICAL INSTRUMENT HAVING A FOURTH EXAMPLE OF A MECHANICAL LOCKOUT ASSEMBLY

Figure 10:
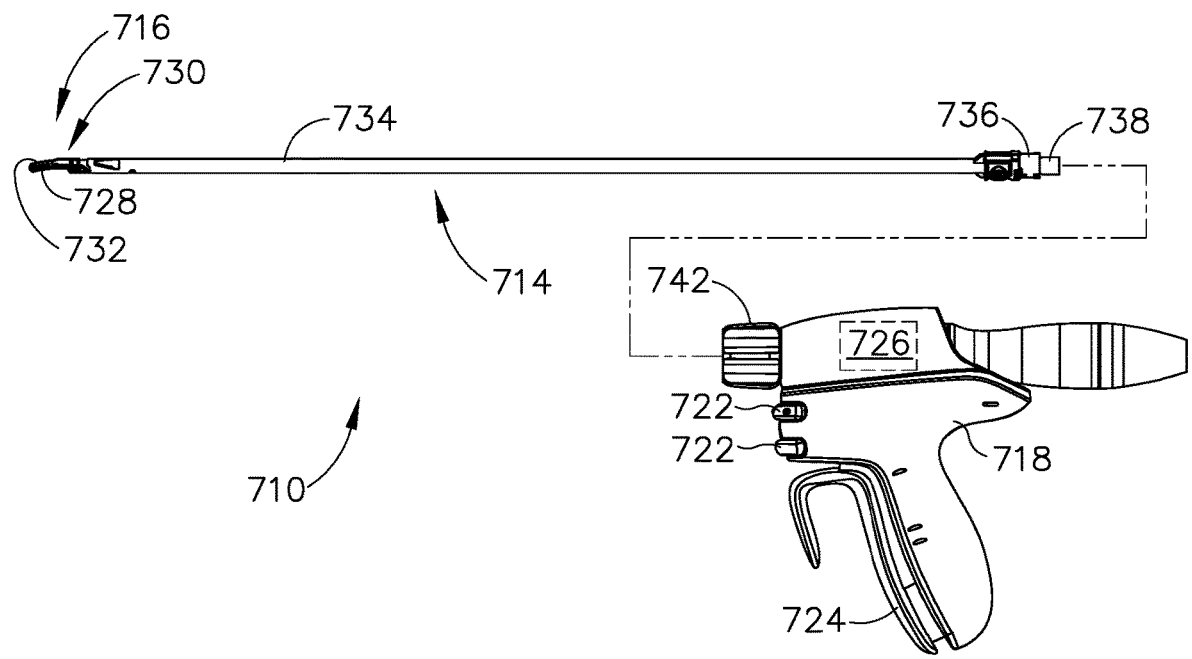
FIG. 10 depicts a schematic side view of a fourth exemplary ultrasonic surgical instrument.
Figure 12:
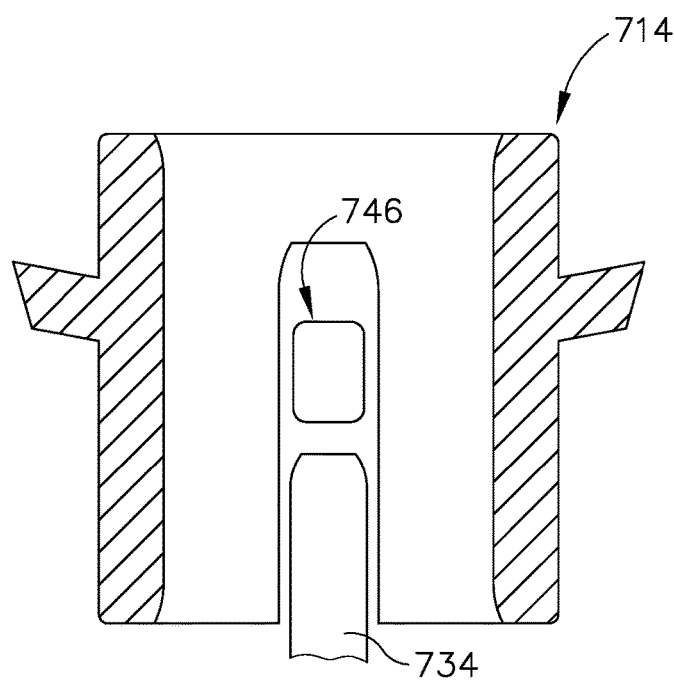
FIG. 12 is a schematic cross-sectional view of FIG. 11A taken along section line 12-12 of FIG. 11A in the locked configuration.

FIGS. 10-12 show a fourth exemplary ultrasonic surgical instrument (710) including a fourth mechanical lockout assembly (744). Instrument (710) of the present example comprises a first modular assembly shown as a handle assembly (712), a second modular assembly shown as a shaft assembly (714), an end effector (716), a body (718), a pistol grip (720), energy control buttons (722), a trigger (724), an ultrasonic transducer (726), an ultrasonic blade (728), a clamp arm (730), a clamp pad (732), an outer tube (734), an inner tube (736), an ultrasonic waveguide (738), and a rotation knob (742).

Figure 11A:
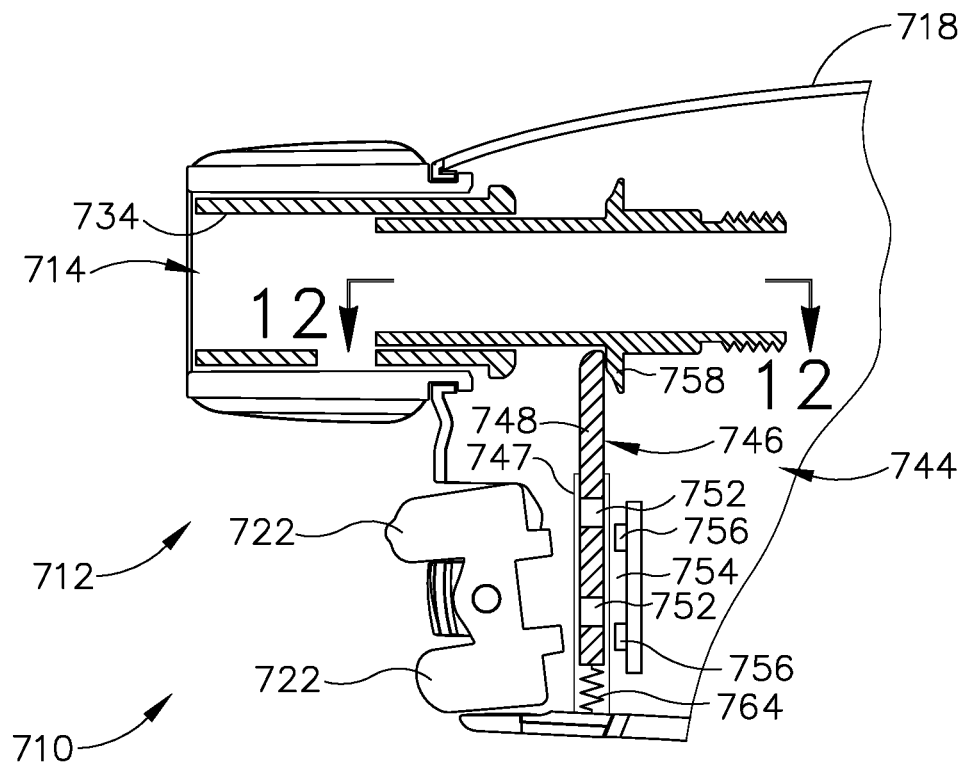
FIG. 11A depicts a schematic side sectional view of the instrument similar to FIG. 10 including a fourth exemplary mechanical lockout assembly in a locked configuration.
Figure 11B:
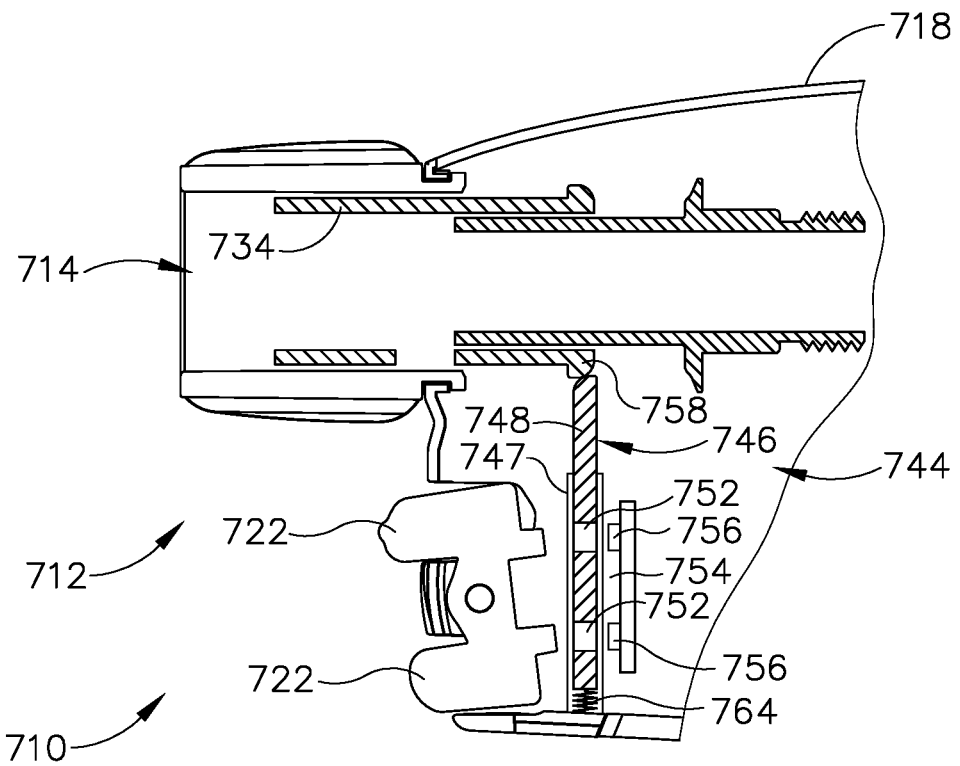
FIG. 11B depicts the schematic side sectional view of the instrument similar to FIG. 11A, but in an unlocked configuration.

FIGS. 11A-11B show instrument (710) as including a mechanical lockout assembly (744). Mechanical lockout assembly (744) includes a barrier (746) that translates between a locked configuration and an unlocked configuration. Barrier (746) may translate within a molded track (747), which may be integrally formed as a unitary piece together with body (718). Barrier (746) includes at least one body portion (748) with at least one aperture (752) being disposed within body portion (748). FIGS. 11A-11B show two apertures (752). Barrier (746) is shown as a lockout slide that is disposed within handle assembly (712). Handle assembly (712) includes energy control buttons (722) separated by a passageway (754) from switches (756).

FIG. 11A shows instrument (710) in the locked configuration, where body portion (748) contacts and translates body portion (750) that is disposed between energy control buttons (722) and switches (756). In other words, when shaft assembly (714), which includes outer tube (734) and clamp arm (730), is not completely coupled with handle assembly (712), barrier (746) prevents the energy control button (722) from being depressed. This prevents switches (756) from activating instrument (710). In the locked configuration, compression spring (764) is in an extended state. In the locked state shown in FIG. 11A, barrier (746) is positioned such that apertures (752) are not interposed between buttons (722) and corresponding switches (756). Barrier (746) thus prevents buttons (722) from activating corresponding switches (756), thereby preventing activation of instrument (710). FIG. 12 depicts a schematic cross-sectional view of FIG. 11A in the locked configuration.

FIG. 11B shows instrument (710) in an unlocked configuration, where apertures (752) are disposed between energy control buttons (722) and switches (756) enabling switches (756) to activate instrument (710). In moving to the unlocked configuration, barrier (746) is pushed downwards into passageway (754) extending between energy control buttons (722) and switches (756). With barrier (746) in a downward position, apertures (752) are positioned between buttons (722) and corresponding switches (756), thereby providing clearance for buttons (722) to activate corresponding switches (756). As shown in FIG. 11B, a tab (758) presses lockout slide down allowing energy control buttons (722) to contact switches (756). Tab (758) may be formed in outer tube (734) or be part of an outer tube overmold. Full coupling of shaft assembly (714) with handle assembly (712) thus causes instrument (710) to move from the locked configuration to the unlocked configuration. In the unlocked configuration, compression spring (764) is in a compressed state. In other words, barrier (746) is spring loaded to return the initial locked configuration, once the shaft assembly (714) is removed.

E. FIFTH EXEMPLARY ULTRASONIC SURGICAL INSTRUMENT HAVING A FIFTH EXAMPLE OF A MECHANICAL LOCKOUT ASSEMBLY

Figure 13A:
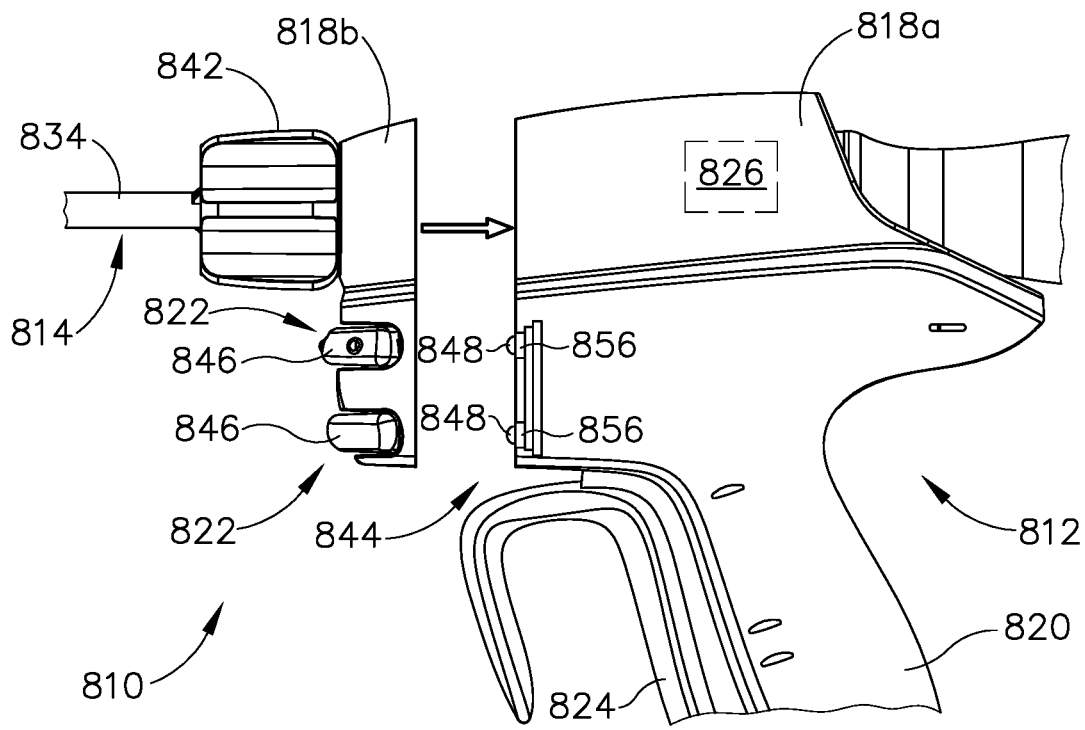
FIG. 13A depicts a schematic side view of a fifth exemplary ultrasonic surgical instrument including a fifth exemplary mechanical lockout assembly in a locked configuration.
Figure 13B:
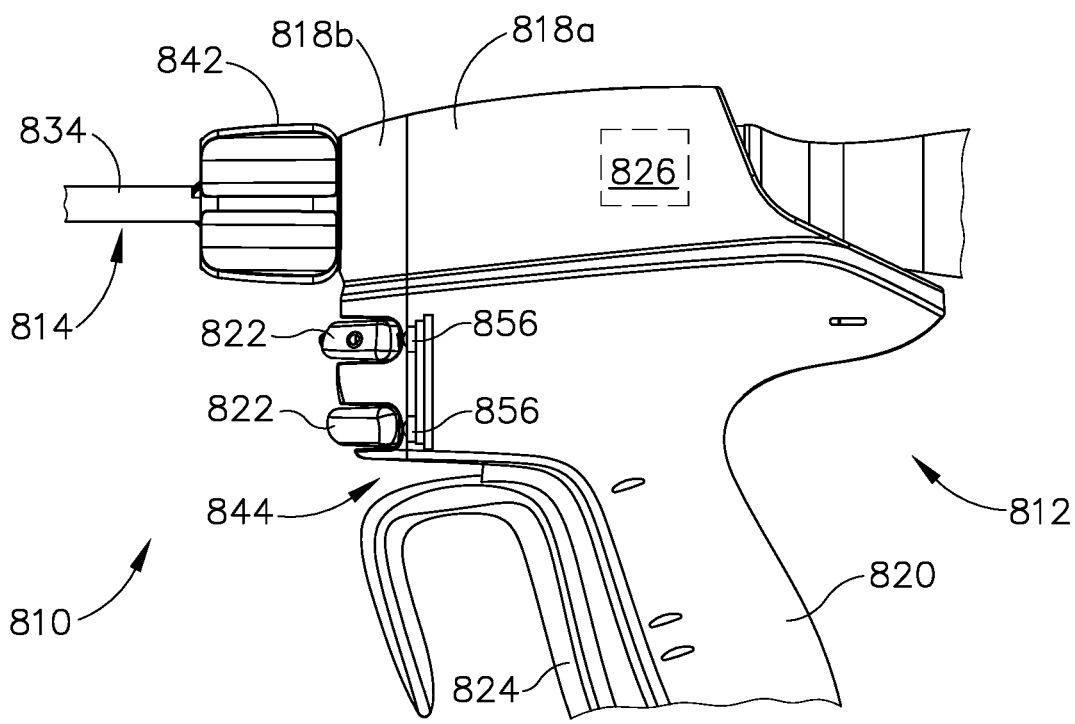
FIG. 13B depicts the schematic side view of the instrument similar to FIG. 13A, but in an unlocked configuration.

FIGS. 13A-13B show a fifth exemplary ultrasonic surgical instrument (810) including a fifth mechanical lockout assembly (844). Instrument (810) of the present example comprises a first modular assembly shown as a first portion of handle assembly (812), a second modular assembly shown as a second portion of handle assembly and a shaft assembly (814), a body (818a, 818b), a pistol grip (820), energy control buttons (822), a trigger (824), an ultrasonic transducer (826), an outer tube (834), and a rotation knob (842).

FIG. 13A shows instrument (810) in a locked configuration, where a mechanical lockout assembly (844) prevents activation of instrument (810) if shaft assembly (814) is not completely coupled with handle assembly (812). Handle assembly (812) may include at least a portion of energy control buttons (822). For example, energy control buttons (822) may be split into shaft and handle portions (846, 848), or have energy control buttons (822) entirely with shaft assembly (814). For example, as shown in FIG. 13A, shaft portions (846) of energy control buttons (822) may be coupled with shaft assembly (814) while handle portions (848) of energy control buttons (822) may be coupled with handle assembly (812). Misalignment of shaft and handle portions (846, 848) of energy control buttons (822) prevents switches (856) from activating instrument (810).

FIG. 13B shows instrument (810) in an unlocked configuration, where shaft assembly (814) is completely coupled with handle assembly (812). In the unlocked configuration, mechanical lockout assembly (844) allows energy control button (822) to contact switch (856), allowing an operator to activate instrument (810). Alignment of shaft and handle portions (846, 848) of energy control buttons (822) enable switches (856) to activate instrument (810). Switches (856), which may be dome switches according to an exemplary embodiment, may be in electrical communication with a printed circuit board ("PCB") and may remain within handle assembly (812). Memory, such as EEPROM, may be disposed within handle assembly (812), and cannot activate energy control buttons (822) without shaft assembly (814) completely installed. Switches (856) may be recessed within handle assembly (812) to prevent unintentional actuation.

F. SIXTH EXEMPLARY ULTRASONIC SURGICAL INSTRUMENT HAVING A SIXTH EXAMPLE OF A MECHANICAL LOCKOUT ASSEMBLY

FIGS. 14A-15D show a sixth exemplary ultrasonic surgical instrument (910) including a sixth mechanical lockout assembly (944). Instrument (910) of the present example comprises a first modular assembly shown as a handle assembly (912), a second modular assembly shown as a shaft assembly (914), a body (918), a pistol grip (920), at least one energy control button (922), a trigger (924), an ultrasonic transducer (926), and an outer tube (934).

As shown in FIGS. 14A-14D, handle assembly (912) includes switches (956) that are configured to be actuated by energy control buttons (922). Mechanical lockout assembly (944) includes a closure lever link (946) operatively coupled with trigger (924) in handle assembly (912). Handle assembly (912) includes stop features (948) that may limit motion of closure lever link (946), if desired. Stop features (948) may be integrally formed as a unitary piece with body (918) of handle assembly (912) or may be distinct components coupled with body (918) of handle assembly (912). As shown in FIGS. 14A-14D, closure lever link (946) is coupled at a first end with body (918) at a first rotation point (950). Closure lever link (946) is coupled at a second end with trigger (924) at a second rotation point (952). Additionally, trigger (924) is coupled with body (918) at a third rotation point (954).

Figure 14A:
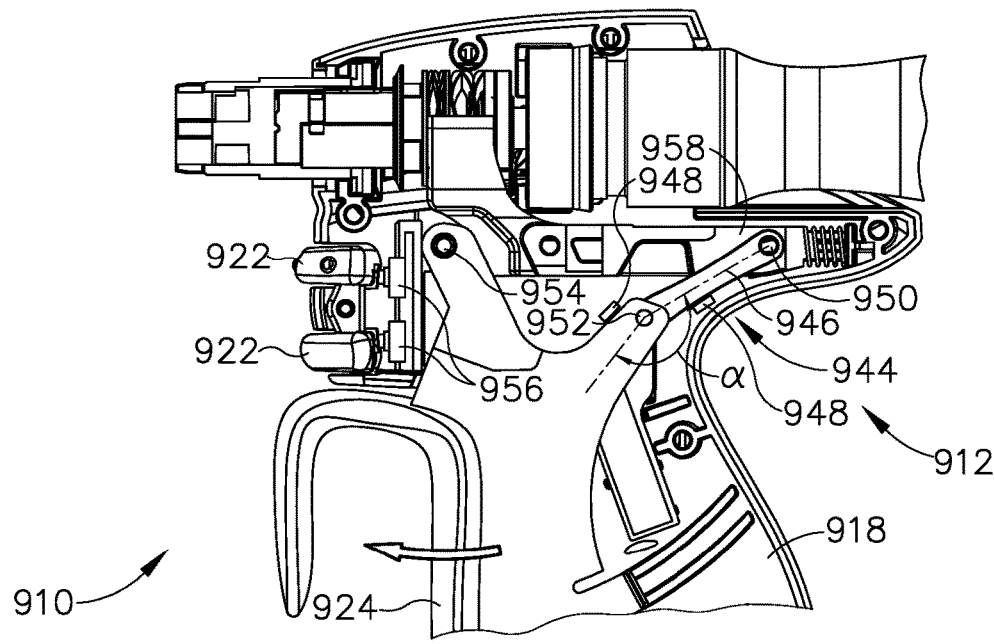
FIG. 14A depicts a schematic side sectional view of a sixth exemplary ultrasonic surgical instrument including a sixth exemplary mechanical lockout assembly in an unlocked configuration.

FIG. 14A shows instrument (910) in an unlocked configuration, with FIG. 15A showing a detailed view of handle assembly (912) where shaft assembly (914) is subsequently inserted therethrough. As shown, in the unlocked configuration, angle alpha ($\alpha$) between first rotation point (950) and a point of trigger (924) is less than 180 degrees. To switch instrument (910) into a locked configuration, trigger (924) is rotated/translated distally as shown by the arrow. It is also envisioned that instrument (910) may be initially in the locked configuration, as will be described in connection with FIG. 15B.

Figure 14B:
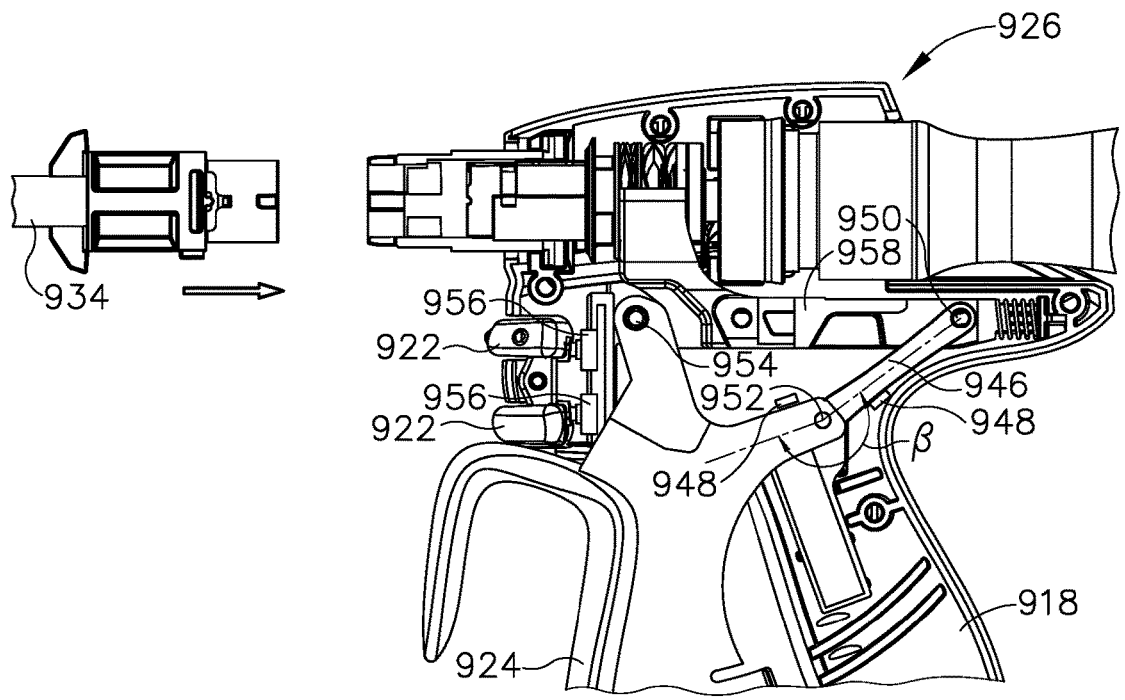
FIG. 14B depicts the schematic side sectional view of the instrument similar to FIG. 14A in a locked configuration.

FIG. 14B shows where the operator pulls closure lever link (946) beyond the unlocked configuration, which functions as the normal operating position, with FIG. 15B showing a detailed view of shaft assembly (914) being actively inserted into handle assembly (912). In the locked configuration when shaft assembly (914) is partially coupled with handle assembly (912), closure lever link (946) is pulled over center in a first direction. Pulling closure lever link (946) over center prevents closure lever link (946) from being rotated closed. As shown in the locked configuration, angle beta ($\beta$) between first rotation point (950) and a point of trigger (924) is greater than 180 degrees. When trigger (924) is effectively locked, this prevents the operator from clamping on tissue with an end effector disposed at a distal end of shaft assembly (914) until shaft assembly (914) is fully seated in handle assembly (912).

Figure 14C:
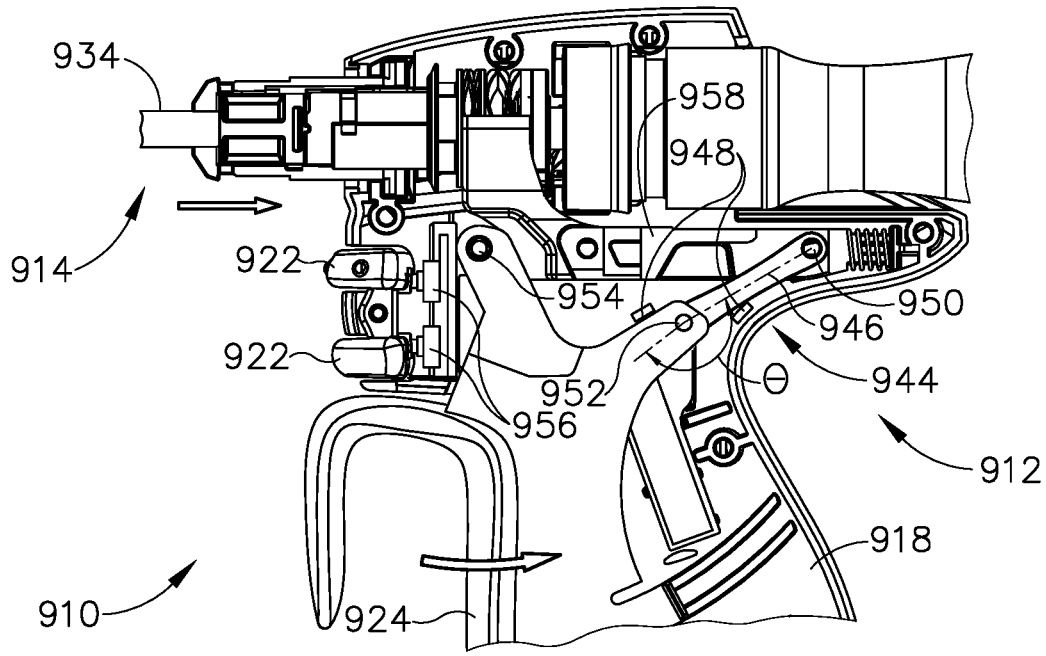
FIG. 14C depicts the schematic side sectional view of the instrument similar to FIG. 14B, but in a second locked configuration.

FIGS. 14C and 15C show a second locked configuration, where shaft assembly (914) is inserted into instrument (910), which pushes yoke (958) proximally, and relieves closure lever link (946) from being over center. Yoke (958) couples trigger assembly of handle with the clamp arm closure driver of shaft assembly (914). As shown in the second locked configuration, angle theta ($\theta$) between first rotation point (950) and a point of trigger (924) is approximately 180 degrees. Mechanical lockout assembly (944) maintains the locked configuration, until shaft assembly (914) is fully seated with handle assembly (912).

Figure 14D:
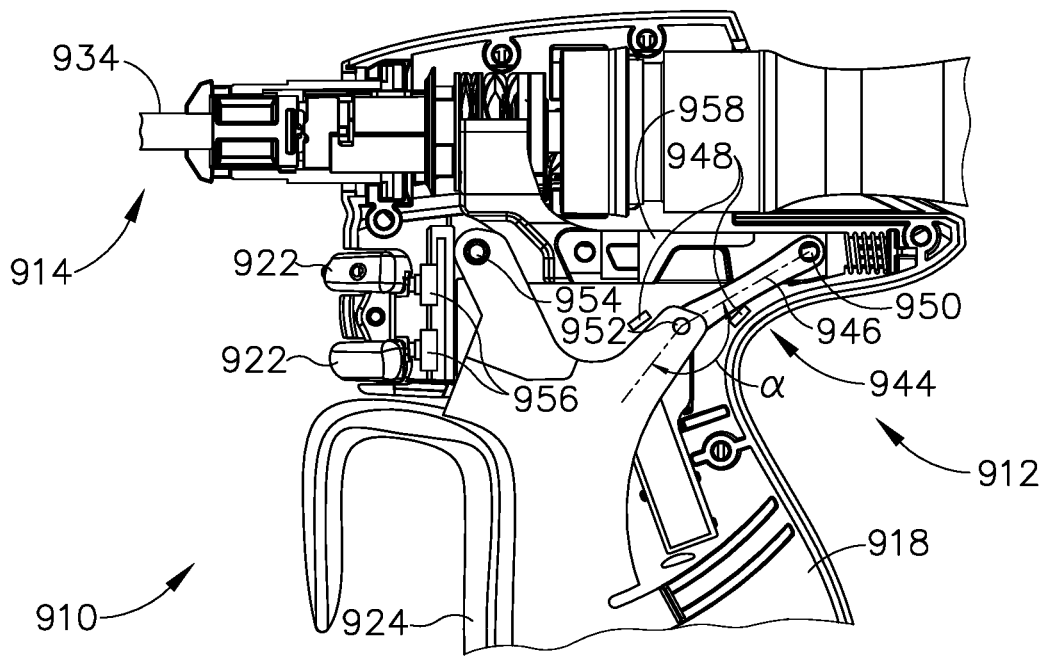
FIG. 14D depicts the schematic side sectional view of the instrument similar to FIG. 14C, but in the unlocked configuration similar to FIG. 14A.
Figure 16:
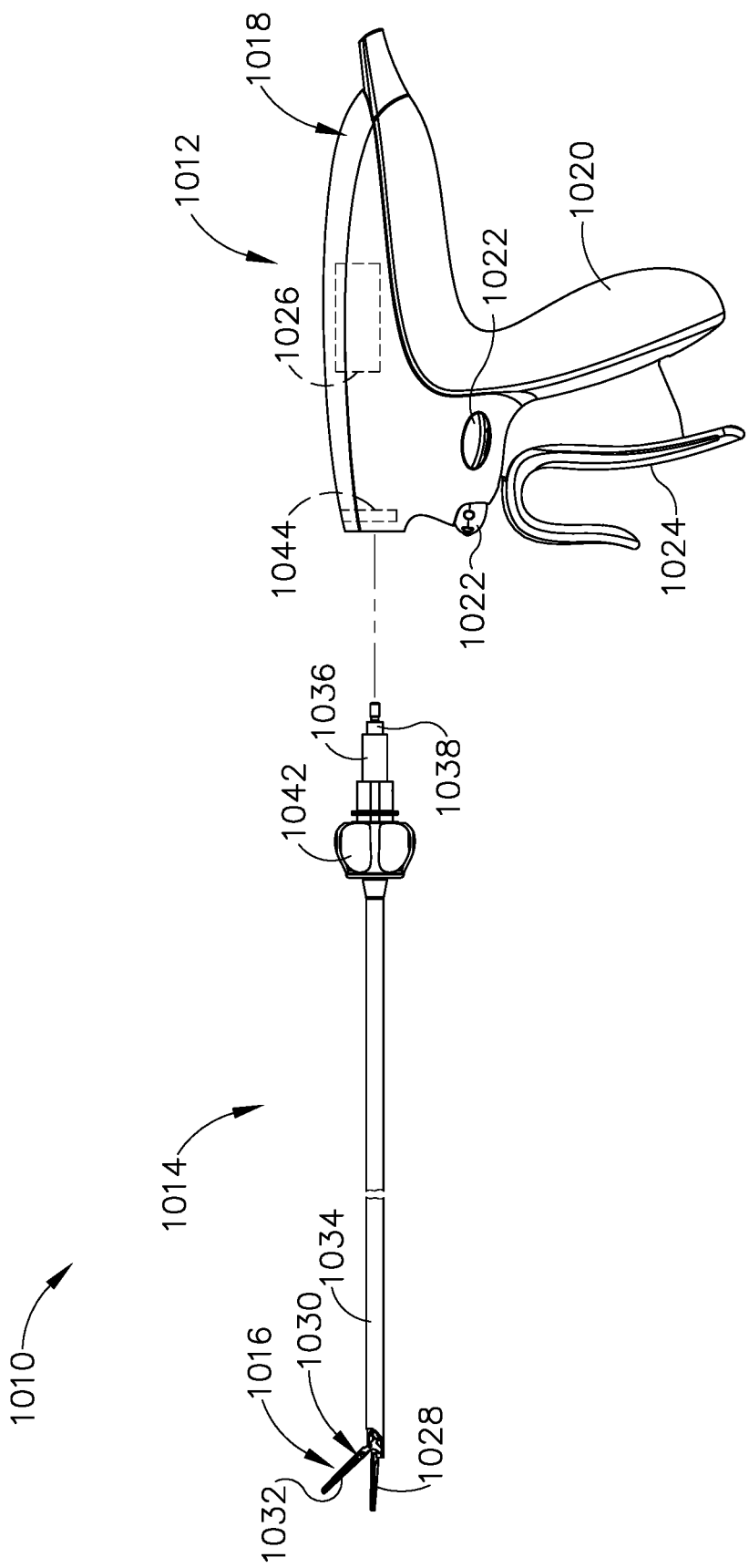
FIG. 16 depicts a schematic partially exploded side view of an seventh exemplary ultrasonic surgical instrument.

FIGS. 14D and 15D show the unlocked configuration when shaft assembly (914) is completely coupled with handle assembly (912). FIG. 14D shows that activation of trigger (924) causes closure lever link (946) to rotate in second direction that is opposite first direction. Once shaft assembly (914) is fully seated in handle assembly (912), trigger (924) is transitioned to the unlocked configuration. This allows trigger (924) to be actuated to thereby actuate a clamp arm of an end effector. Mechanical lockout assembly (944) effectively locks out use of a clamp arm assembly. In the unlocked configuration, angle alpha ($\alpha$) between first rotation point (950) and a point of trigger (924) is less than 180 degrees.

G. SEVENTH EXEMPLARY ULTRASONIC SURGICAL INSTRUMENT HAVING A SEVENTH EXAMPLE OF A MECHANICAL LOCKOUT ASSEMBLY

FIGS. 16-18C show a seventh exemplary ultrasonic surgical instrument (1010) including a seventh mechanical lockout assembly (1044). Instrument (1010) of the present example comprises a first modular assembly shown as a handle assembly (1012), a second modular assembly shown as a shaft assembly (1014), an end effector (1016), a body (1018), a pistol grip (1020), energy control buttons (1022), a trigger (1024), an ultrasonic transducer (1026), an ultrasonic blade (1028), a clamp arm (1030), a clamp pad (1032), an outer tube (1034), an inner tube (1036), an ultrasonic waveguide (1038), and a rotation knob (1042).

Figure 17A:
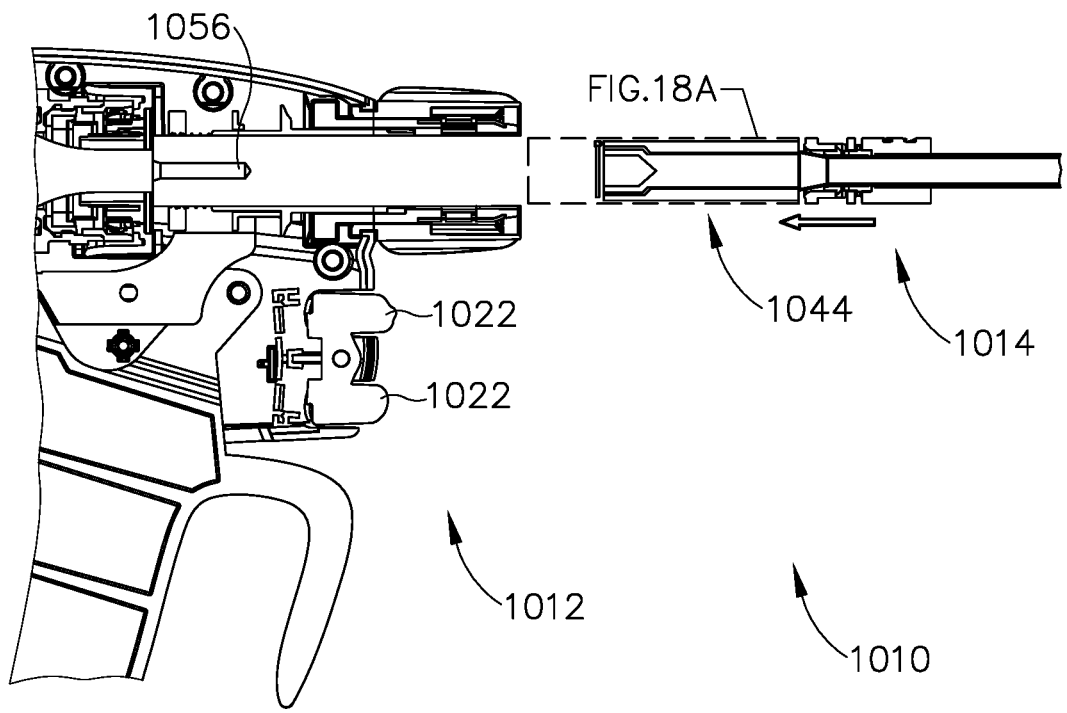
FIG. 17A depicts a schematic sectional view of the instrument similar to FIG. 16 including an seventh exemplary mechanical lockout assembly in a locked configuration.
Figure 17B:
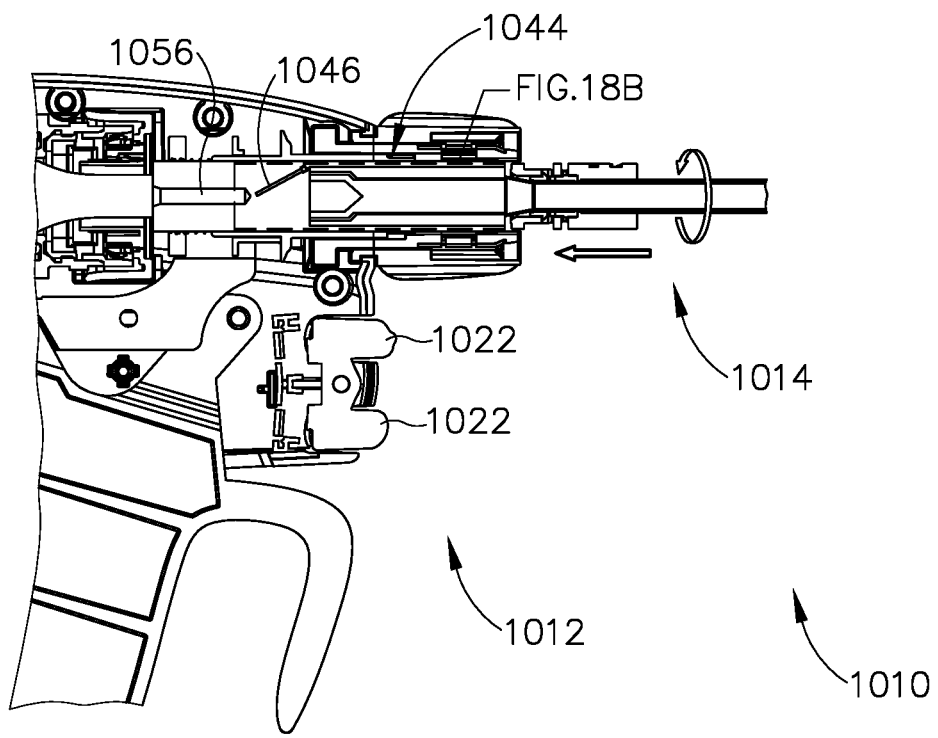
FIG. 17B depicts the schematic sectional view of the instrument similar to FIG. 17A, but moving from a locked configuration to an unlocked configuration.
Figure 17C:
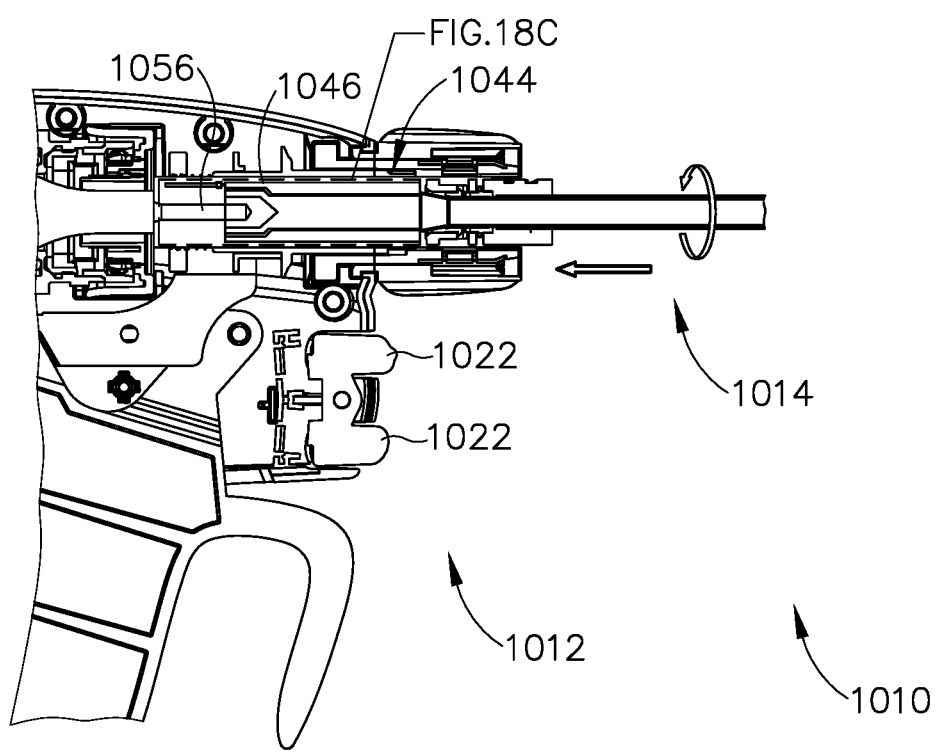
FIG. 17C depicts the schematic sectional view of the instrument similar to FIG. 17B, but in the unlocked configuration.
Figure 18A:
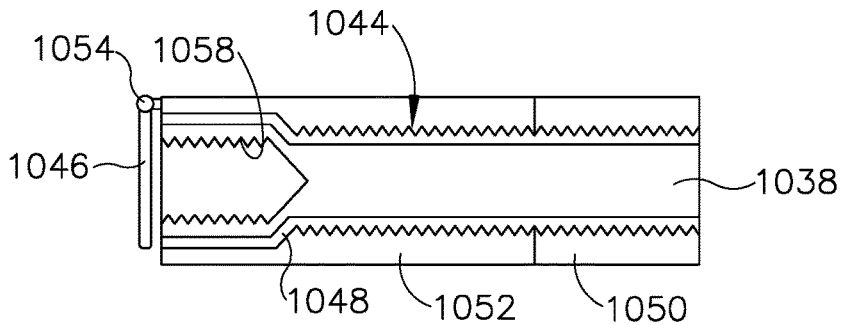
FIG. 18A depicts a schematic enlarged side sectional view of the mechanical lockout assembly similar to FIG. 17A in the locked configuration.

FIGS. 17A-17C show instrument (1010) as including a mechanical lockout assembly (1044). Mechanical lockout assembly (1044) includes a one-way door (1046) that is configured to be opened by coupling handle assembly (1012) with shaft assembly (1014). As shown in FIGS. 17A-17C, mechanical lockout assembly (1044) is coupled with shaft assembly (1014), such that shaft assembly (1014) and mechanical lockout assembly (1044) are coupled together, however, this is not required. FIGS. 17A and 18A show shaft assembly (1014) approaching handle assembly (1012), with one-way door (1046) blocking access to threaded bore (1058) at the proximal end of acoustic waveguide (1038) of shaft assembly (1014).

Figure 18B:
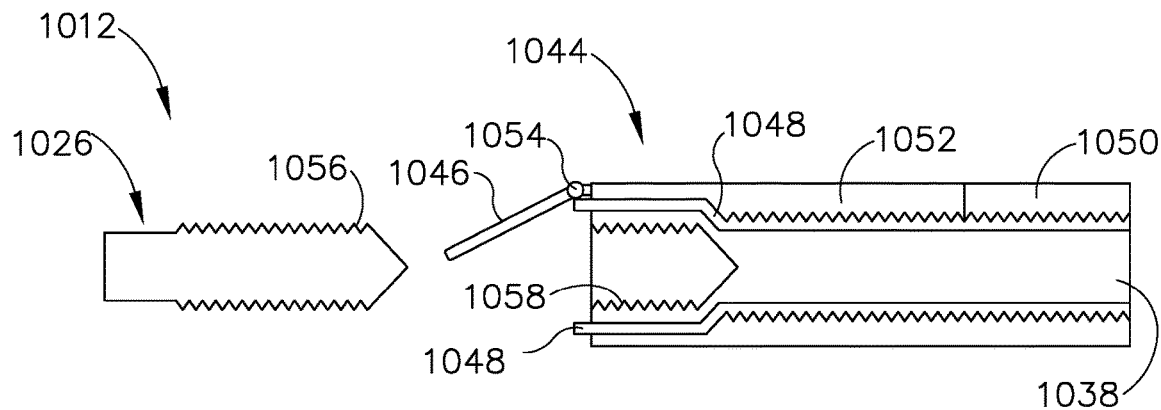
FIG. 18B depicts the schematic enlarged side sectional view of the mechanical lockout assembly similar to FIG. 17B transitioning from the locked configuration to the unlocked configuration.

FIGS. 17B and 18B show shaft assembly (1014) partially coupled with handle assembly (1012), with one-way door (1046) still preventing threaded stud (1056) of ultrasonic transducer (1026) from reaching threaded bore (1058) at the proximal end of acoustic waveguide (1038). In moving between a locked and an unlocked configuration, translatable jacket (1048) translates relative to one-way door (1046) pushing one-way door (1046) to the unlocked configuration (shown in FIGS. 17C and 18C) allowing complete coupling of threaded stud (1056) with threaded bore (1058), thereby completing an acoustic coupling between ultrasonic transducer (1026) and ultrasonic waveguide (1038).

As shown, linear translation of outer tube (1034) of shaft assembly (1014) relative to translatable jacket (1048) opens one-way door (1046). As shown, outer tube (1034) includes a rotary component (1050) and a yoke (1052), however, rotary component (1050) and yoke (1052) may be integrally formed as a unitary piece or fixably coupled together using a variety of known attachment methods. As shown, rotation of rotary component (1050) of outer tube (1034) causes yoke (1052) of outer tube (1034) and translatable jacket (1048) to translate towards handle assembly (1012). Yoke (1052) may be threadably coupled with rotary component (1050), with yoke (1052) being keyed to shaft assembly (1014), such that yoke (1052) translates relative to shaft assembly (1014) without rotating relative to shaft assembly (1014). Rotation of rotary component (1050) drives yoke (1052) proximally, allowing translatable jacket (1048) to translate proximally, which in turn allows one-way door (1046) to rotate open at a hinge point (1054).

Figure 18C:
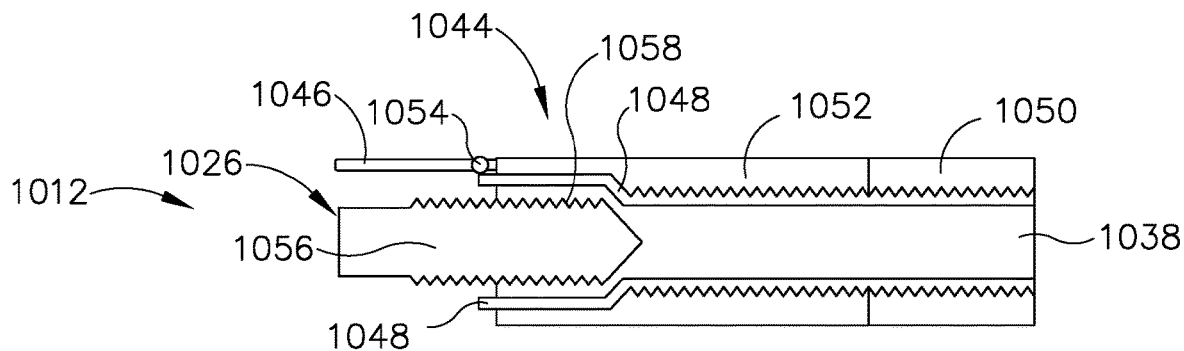
FIG. 18C depicts the schematic enlarged side sectional view of the mechanical lockout assembly similar to FIG. 17C in the unlocked configuration.
Figure 19:
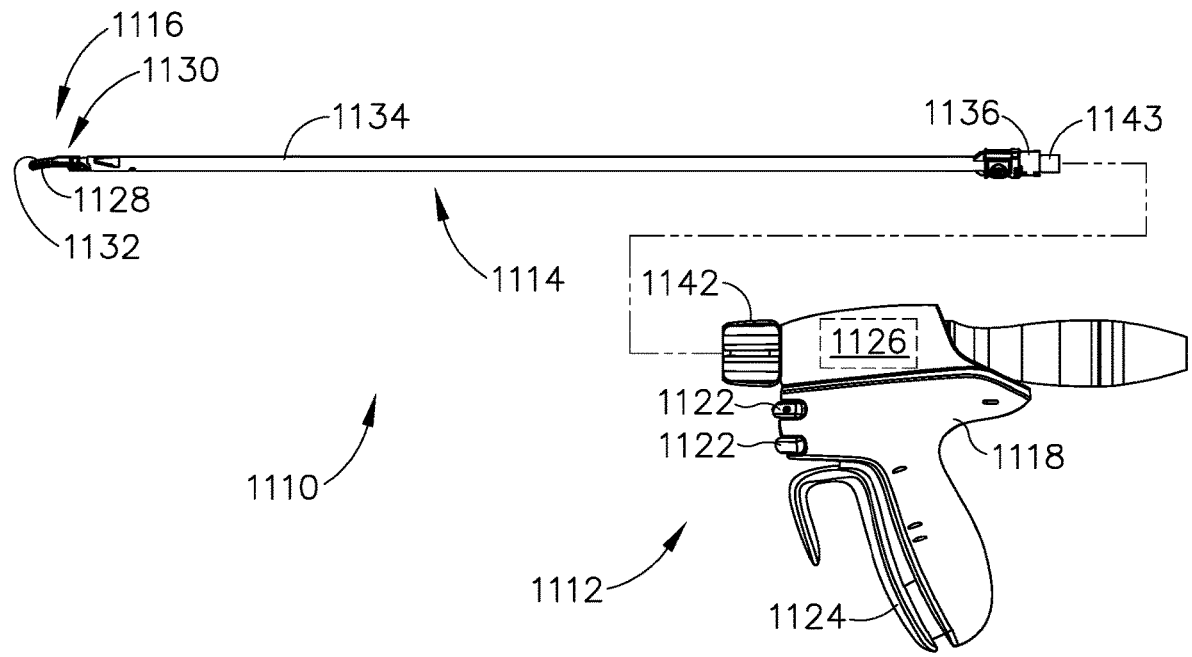
FIG. 19 depicts a schematic side view of an eighth exemplary ultrasonic surgical instrument.

FIGS. 17C and 18C show the unlocked configuration where shaft assembly (1014) is completely coupled with handle assembly (1012), and with transducer (1026) fully coupled with waveguide (1038), thereby allowing ultrasonic activation of ultrasonic blade (1028). FIGS. 17C and 18C show that once one-way door (1046) is open, externally threaded stud (1056) of ultrasonic transducer (1026) may be threadably coupled with an internally threaded proximal recess (1058) of ultrasonic waveguide (1038). In other words, once one-way door (1046) is open and outer tube (1034) is fully translated, ultrasonic transducer (1026) is able to acoustically couple with ultrasonic waveguide (1038). One-way door (1046) ensures that the acoustic drivetrain may only be assembled when shaft assembly (1014) is completely coupled with handle assembly (1012).

For instrument (1010), which includes clamp arm (1030) that is assembled by the operator to handle assembly (1012), it is beneficial that clamp arm (1030) be precisely aligned with ultrasonic blade (1028). Mechanical lockout assembly (1044) incorporates a means to lock out the acoustic drivetrain, so that ultrasonic blade (1028) cannot be activated by energy control buttons (1022) until shaft assembly (1014) is completely coupled with handle assembly (1012). Additionally, if there is not full rotary engagement, translatable jacket (1048) falls short and cannot open one-way door (1046), and as a result, handle assembly (1012) contacts one-way door (1046) and does not thread ultrasonic waveguide (1038). This prevents use of trigger (1024) that drives the clamp arm (1030) and champ pad (1032) toward the ultrasonic blade (1028), which provides tactile feedback to the operator of the inoperability of instrument (1010) due to being in the locked configuration.

H. EIGHTH EXEMPLARY ULTRASONIC SURGICAL INSTRUMENT HAVING AN EIGHTH EXAMPLE OF A MECHANICAL LOCKOUT ASSEMBLY

FIGS. 19-21D show an eighth exemplary ultrasonic surgical instrument (1110) including an eighth mechanical lockout assembly (1144). Instrument (1110) of the present example comprises a first modular assembly shown as a handle assembly (1112), a second modular assembly shown as a shaft assembly (1114), an end effector (1116), a body (1118), a pistol grip (1120), energy control buttons (1122), a trigger (1124), an ultrasonic transducer (1126), an ultrasonic blade (1128), a clamp arm (1130), a clamp pad (1132), an outer tube (1134), an inner tube (1136), a rotation knob (1142), and a shaft coupler (1143).

Figure 20:
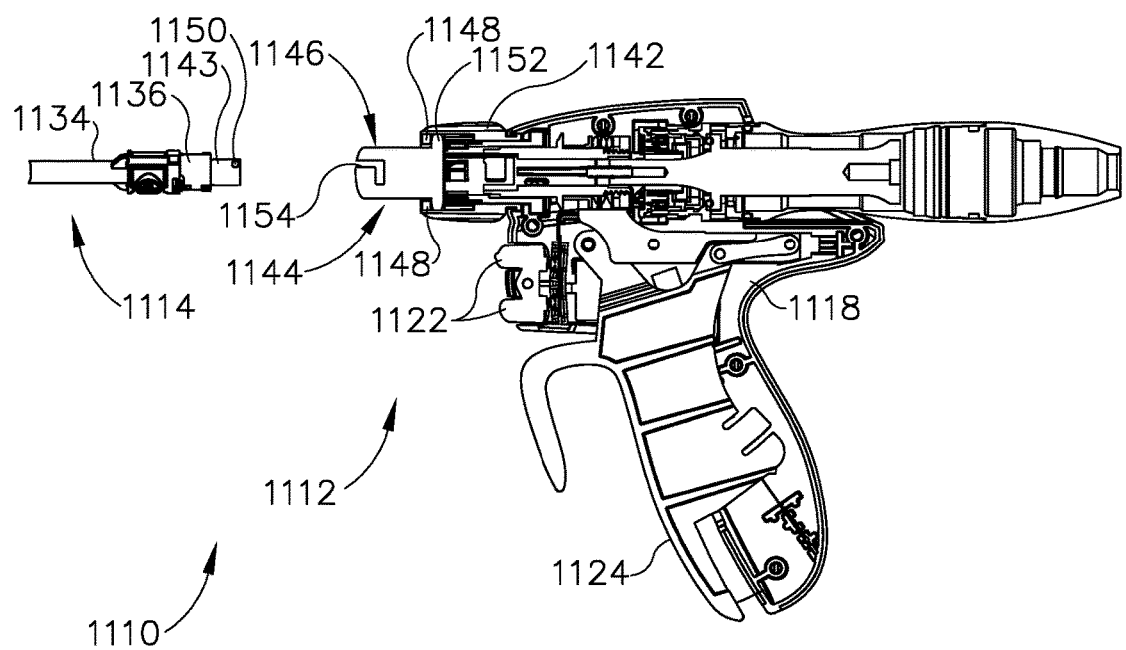
FIG. 20 depicts a schematic side sectional view of the instrument of FIG. 19 including an eighth exemplary mechanical lockout assembly in a locked configuration.

FIG. 20 shows that instrument (1110) includes a mechanical lockout assembly (1144). Mechanical lockout assembly (1144) includes a coupling device (1146) operatively coupled to handle assembly (1112) using a retention member (1148) that restricts distal translation of a head portion (1152) of coupling device (1146). More specifically, since coupling device (1146) translates longitudinally to communicate a clamp arm closure motion from trigger (1124) to clamp arm actuator of shaft assembly (1114), coupling device (1146) subsequently translates proximally from the position shown in FIG. 20. Subsequently, coupling device (1146) translates distally back to the position shown in FIG. 20. In this manner, retention member (1148) restricts distal translation of coupling device (1146). Clamp arm actuating member translates relative to the remainder of shaft assembly (1114) to drive pivotal movement of clamp arm (1130) toward and away from ultrasonic blade (1128). As shaft assembly (1114) couples with handle assembly (1112), projection (1150) that is shown integral with clamp arm actuating member of shaft assembly (1114), enters track (1154) to suitably couple shaft assembly (1114) with handle assembly (1112).

FIGS. 21A-21D show four exemplary coupling devices (1156, 1158, 1160, 1162), configured to be used with mechanical lockout assembly (1144) of instrument (1110). Coupling devices (1146, 1156, 1158, 1160, 1162) translate longitudinally in response to pivotal movement of trigger (1124). Coupling devices (1146, 1156, 1158, 1160, 1162) also couple trigger (1124) with the clamp arm closure actuator of shaft assembly (1114). Clamp arm closure actuator includes projection (1150). Thus, if projection (1150) of shaft assembly (1114) is fully seated in coupling device (1146, 1156, 1158, 1160, 1162), the clamp arm closure actuator will translate and thereby drive clamp arm (1130) toward and away from ultrasonic blade (1128), based on translation of coupling device (1146, 1156, 1158, 1160, 1162) as driven by trigger (1124). If projection (1150) of shaft assembly (1114) is not fully seated in coupling device (1146, 1156, 1158, 1160, 1162), coupling device (1146, 1156, 1158, 1160, 1162) still translates in response to pivotal movement of trigger (1124). However, the translational movement of the coupling device (1146, 1156, 1158, 1160, 1162) is not be communicated to the clamp arm closure actuator. Thus, clamp arm (1130) does not move at all in response to movement of trigger (1124). Coupling devices (1146, 1156, 1158, 1160, 1162) move proximally to actuate clamp arm (1130).

As will be described below, each coupling device (1156, 1158, 1160, 1162) includes a guide track (1164, 1166, 1168, 1170) configured to engage with projection (1150) shown in FIG. 20 of shaft assembly (1114). Guide tracks (1154, 1164, 1166, 1168, 1170) of respective coupling devices (1146, 1156, 1158, 1160, 1162) are configured to translate and rotate shaft assembly (1114) using the interaction between projection (1150) and guide track (1154, 1164, 1166, 1168, 1170) from the locked configuration when shaft assembly (1114) is partially coupled with handle assembly (1112) to the unlocked configuration when shaft assembly (1114) is completely coupled with handle assembly (1112).

Figure 21A:
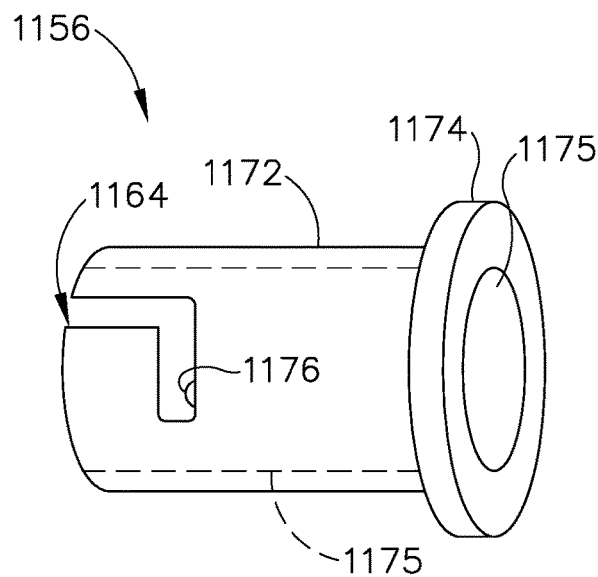
FIG. 21A depicts a schematic perspective view of a first alternative embodiment of a coupling device configured to be used with the instrument of FIG. 19.

FIG. 21A shows a coupling device (1156) with a guide track (1164) disposed within a body portion (1172) and a head portion (1174) that is configured to be retained by retention member (1148), and an aperture (1175) extending therethrough. Coupling device (1156) is similar to coupling device (1146) shown in FIG. 20, however, coupling device (1156) additionally includes a detent (1176) to guide track (1164) to ensure that trigger (1124) and clamp arm (1130) are non-responsive until projection (1150) is fully seated and fully rotated. If projection (1150) is captured by detent (1176), then the translation of coupling device (1156) will be communicated to the clamp arm actuator of shaft assembly (1114), such that the clamp arm (1130) will close in response to pivoting of trigger (1124). Detent (1176) provides tactile feedback to the operator indicating to the operator that shaft assembly (1114) is fully coupled; and to prevent inadvertent decoupling of the shaft assembly (1114) after shaft assembly (1114) is fully coupled.

Figure 21B:
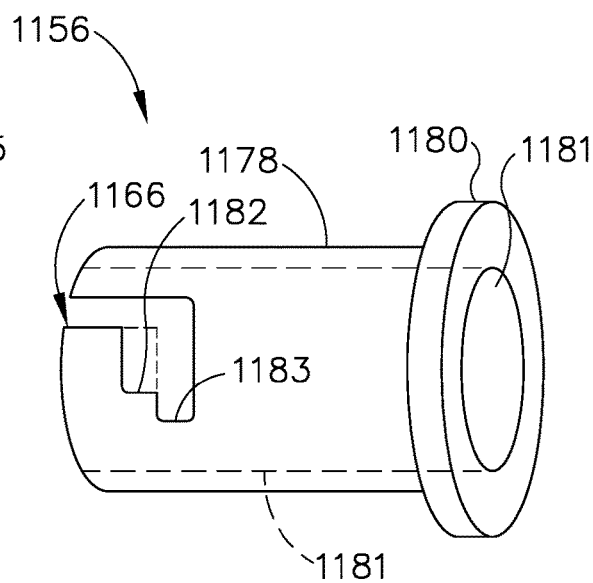
FIG. 21B depicts a schematic perspective view of a second alternative embodiment of a coupling device configured to be used with the instrument of FIG. 19.
Figure 21C:
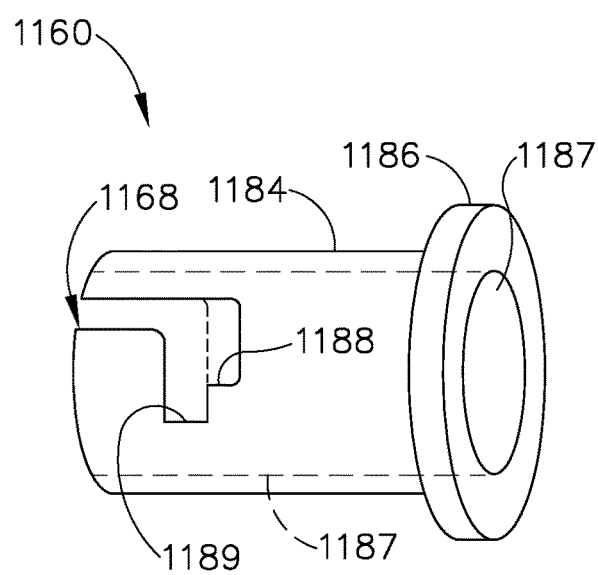
FIG. 21C depicts a schematic perspective view of a third alternative embodiment of a coupling device configured to be used with the instrument of FIG. 19.
Figure 21D:
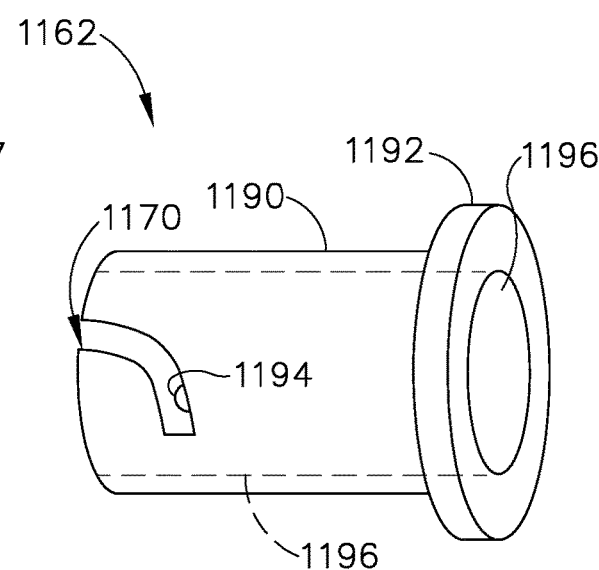
FIG. 21D depicts a schematic perspective view of a fourth alternative embodiment of a coupling device configured to be used with the instrument of FIG. 19.
Figure 22:
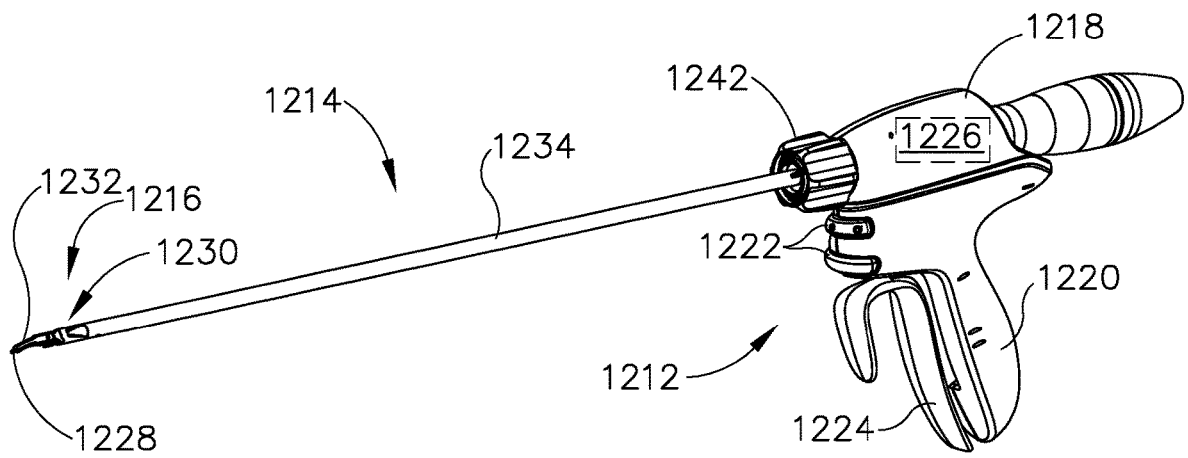
FIG. 22 depicts a schematic perspective view of a ninth exemplary ultrasonic surgical instrument.

FIGS. 21B-21D show three exemplary embodiments of track patterns (1166, 1168, 1170) that result in various changes to the opening/closing of clamp arm (1130) during operation when shaft assembly (1114) is not completely coupled with handle assembly (1112). FIG. 21B shows a coupling device (1158) as including a guide track (1166) disposed within a body portion (1178) and a head portion (1180) that is configured to be retained by retention member (1148), and an aperture (1181) extending therethrough. FIG. 21B shows coupling device (1158) as including an extra relief portion (1182) prior to seating position, which allows clamp arm (1130) to open but not to close, thereby alerting the operator of a potential misalignment. As shown, extra relief portion (1180) is longer than the length of travel.

With continued reference to FIG. 21B, if shaft assembly (1114) is not fully coupled, projection (1150) of shaft assembly (1114) will be in relief portion (1182). If projection (1150) of shaft assembly (1114) is in relief portion (1182), then translation of coupling device (1158) will not be communicated to the clamp arm actuator of shaft assembly (1114), such that clamp arm (1130) will not close in response to pivoting of trigger (1124). If shaft assembly (1114) is fully coupled, projection (1150) will be seated in seat (1183). If projection (1150) captured by seat (1183), then the translation of coupling device (1158) will be communicated to the clamp arm actuator of shaft assembly (1114), such that clamp arm (1130) will open, but not close, in response to pivoting of trigger (1124). Proximal movement of the clamp arm actuator of shaft assembly (1114) provides pivotal movement of clamp arm (1130) toward ultrasonic blade (1128).

FIG. 21C shows a coupling device (1160) with a guide track (1168) disposed within a body portion (1184) and head portion (1186) that is configured to be retained by retention member (1148), and an aperture (1187) extending therethrough. FIG. 21B shows coupling device (1158) as including an extra relief portion (1188) positioned beyond the normal seating position allowing clamp arm (1130) to close if not fully rotated, but not allowing clamp arm (1130) to return back, thereby alerting the operator of a potential misalignment. As shown, extra relief portion (1180) is longer than the length of travel. Distal movement of the clamp arm actuator of shaft assembly (1114) provides pivotal movement of clamp arm (1130) toward ultrasonic blade (1128).

With continued reference to FIG. 21C, if shaft assembly (1114) is not fully coupled, projection (1150) of shaft assembly (1114) will be in relief portion (1188). If projection (1150) of shaft assembly (1114) is in relief portion (1188), the translation of coupling device (1160) will not be communicated to the clamp arm actuator of shaft assembly (1114), such that clamp arm (1130) will not open in response to pivoting of trigger (1124). If shaft assembly (1114) is fully coupled, projection (1150) will be seated in seat (1189). If projection (1150) is captured by seat (1189), then the translation of coupling device (1160) will be communicated to the clamp arm actuator of shaft assembly (1114), such that clamp arm (1130) will close, but not open, in response to pivoting of trigger (1124). Proximal movement of the clamp arm actuator of shaft assembly (1114) provides pivotal movement of clamp arm (1130) toward ultrasonic blade (1128).

FIG. 21D shows a coupling device (1162) as including a guide track (1170) disposed within a body portion (1190) and head portion (1192) that is configured to be retained by retention member (1148), and an aperture (1196) extending therethrough. FIG. 21D shows guide track (1170) as being angled, so as to rotate while advancing. To be fully seated, projection (1150) of shaft coupler (1143) is fully rotated on coupling device (1162). Coupling device (1162) may additionally include a stop member (1194) in guide track (1170) to ensure that trigger (1124) and clamp arm (1130) are non-responsive until projection (1150) is fully seated and fully rotated, such that instrument (1110) is switched from the locked configuration to the unlocked configuration. Similar to detent (1176) shown in FIG. 21A, detent (1194) provides tactile feedback to the operator and prevents inadvertent decoupling. Unlike the FIG. 21A the curved configuration of guide track (1170) causes the coupling device to release projection (1150) if the operator actuates trigger (1124), thereby translating coupling device (1162) if projection (1150) is not fully seated behind detent (1194). Coupling device (1162) moves proximally to actuate clamp arm (1130).

Instrument (1110) prevents outer shaft (1134) from moving forwards/backwards, thereby preventing closing of clamp arm (1130) when shaft assembly (1114) is not fully rotated into position. Mechanical lockout assembly (1144) and its various coupling devices (1146, 1156, 1158, 1160, 1162) prevent responsiveness of clamp arm (1130) to movement of trigger until shaft assembly (1114) is fully seated. Mechanical lockout assembly (1144) using a shaft coupler (1143) with projection (1150) couples with guide tracks (1154, 1164, 1166, 1168, 1170) of respective coupling devices (1146, 1156, 1158, 1160, 1162) providing immediate and clear feedback to the operator of a misalignment between shaft assembly (1114) and handle assembly (1112).

I. NINTH EXEMPLARY ULTRASONIC SURGICAL INSTRUMENT HAVING A NINTH EXAMPLE OF A MECHANICAL LOCKOUT ASSEMBLY

FIGS. 22-28 show a ninth exemplary ultrasonic surgical instrument (1210) including a ninth mechanical lockout assembly (1244). Instrument (1210) of the present example comprises a first modular assembly shown as a handle assembly (1212), a second modular assembly shown as a shaft assembly (1214), an end effector (1216), a body (1218), a pistol grip (1220), energy control buttons (1222), a trigger (1224), an ultrasonic transducer (1226), an ultrasonic blade (1228), a clamp arm (1230), a clamp pad (1232), an outer tube (1234), an inner tube (1236), and a rotation knob (1242).

Figure 23:
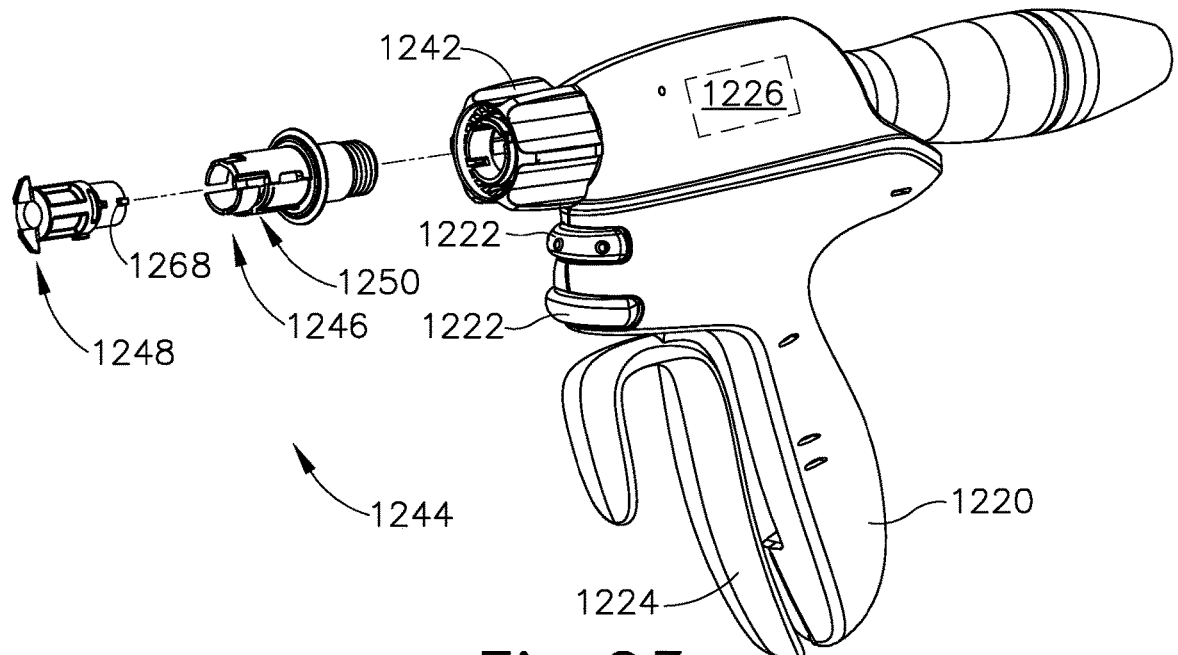
FIG. 23 depicts a schematic partially exploded perspective of the instrument of FIG. 22 including a ninth exemplary mechanical lockout assembly.

FIG. 23 shows instrument (1210) as including a mechanical lockout assembly (1244). As shown, mechanical lockout assembly (1244) includes an outer tube collar (1246) and a bayonet collar (1248), and a rotation collar (1249) (see FIG. 28). Outer tube collar (1246) is integrated into handle assembly (1212). Outer tube collar (1246) may rotate within handle assembly (1212), and may also translate within handle assembly (1212). Outer tube collar (1246) is part of a clamp arm drive assembly that couples trigger (1224) of handle assembly (1212) with outer tube (1234) of shaft assembly (1214). When trigger (1224) is actuated, outer tube collar (1246) translates longitudinally. When outer tube collar (1246) translates, the translation of outer tube collar (1246) is communicated to outer tube (1234) of shaft assembly (1214). When outer tube (1234) of shaft assembly (1214) translates, clamp arm (1230) pivots toward and away from ultrasonic blade (1228). Bayonet collar (1248) may be removably coupled with shaft assembly (1214), and is fixedly secured to the proximal end of outer tube (1234) of shaft assembly (1214). Rotation collar (1249) (see FIG. 28) is integrated into handle assembly (1212) as part of rotation knob (1242) that rotates entire shaft assembly (1214) relative to handle assembly (1212). Rotation collar (1249) rotates relative to handle assembly (1212), but does not translate relative to handle assembly (1212).

Figure 24:
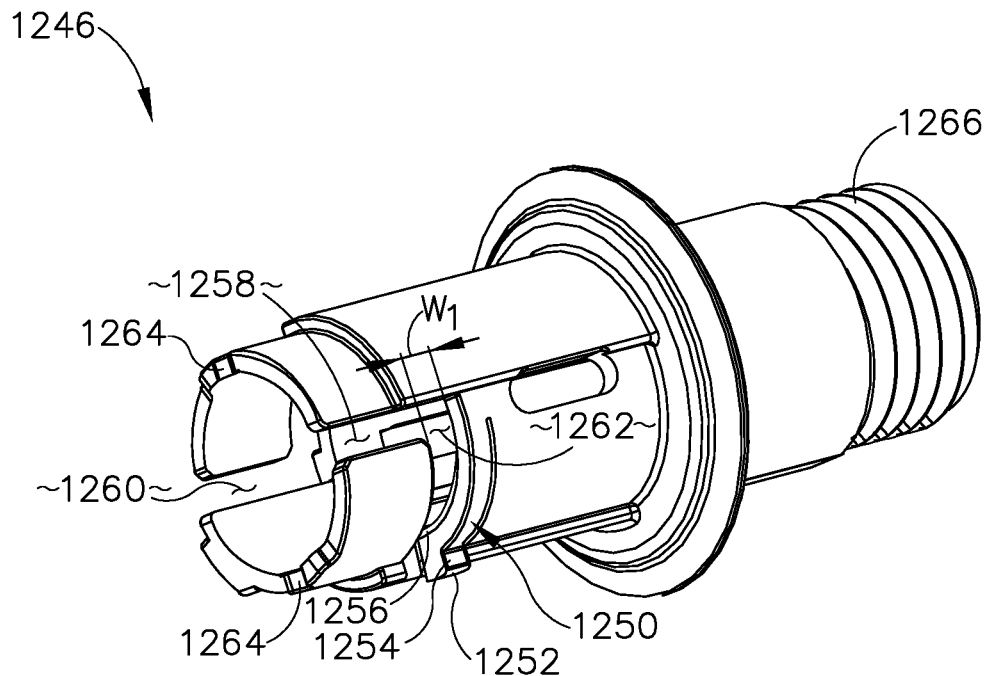
FIG. 24 depicts a schematic enlarged perspective view of an outer tube collar of the mechanical lockout assembly of FIG. 23.

FIG. 24 shows outer tube collar (1246) as including a spring leg (1250) that includes a distal end (1252). Distal end (1252) of spring leg (1250) includes a resilient interference tab (1254) with a contact surface (1255). Spring leg (1250) also includes a cam surface (1256) that acts as a ramp, which will be discussed in greater detail below with reference to FIGS. 26A-27C. Outer tube collar (1246) also includes first and second passageways (1258, 1260), which extend in a generally longitudinal direction relative to outer tube collar (1246), and a third passageway (1262) having a width of W1 that extends generally transverse to the longitudinal direction of outer tube collar (1246). A fourth passageway, similar to third passageway (1262), is hidden from view. Outer tube collar (1246) also includes cutouts (1264) as will be discussed with reference to FIG. 26B. Outer tube collar (1246) may be threadably coupled to a portion of clamp arm drivetrain using threaded portion (1266). Thus, outer tube collar (1246) translates with clamp arm drivetrain.

Figure 25:
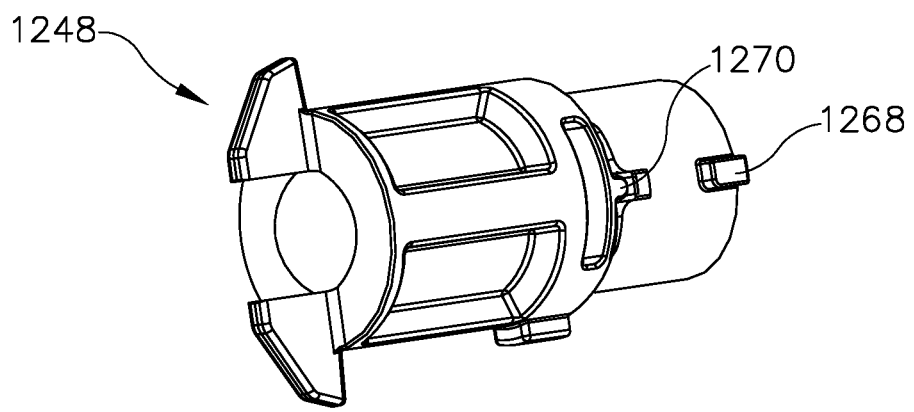
FIG. 25 depicts a schematic enlarged perspective view of a bayonet collar of the mechanical lockout assembly of FIG. 23.
Figure 26C:
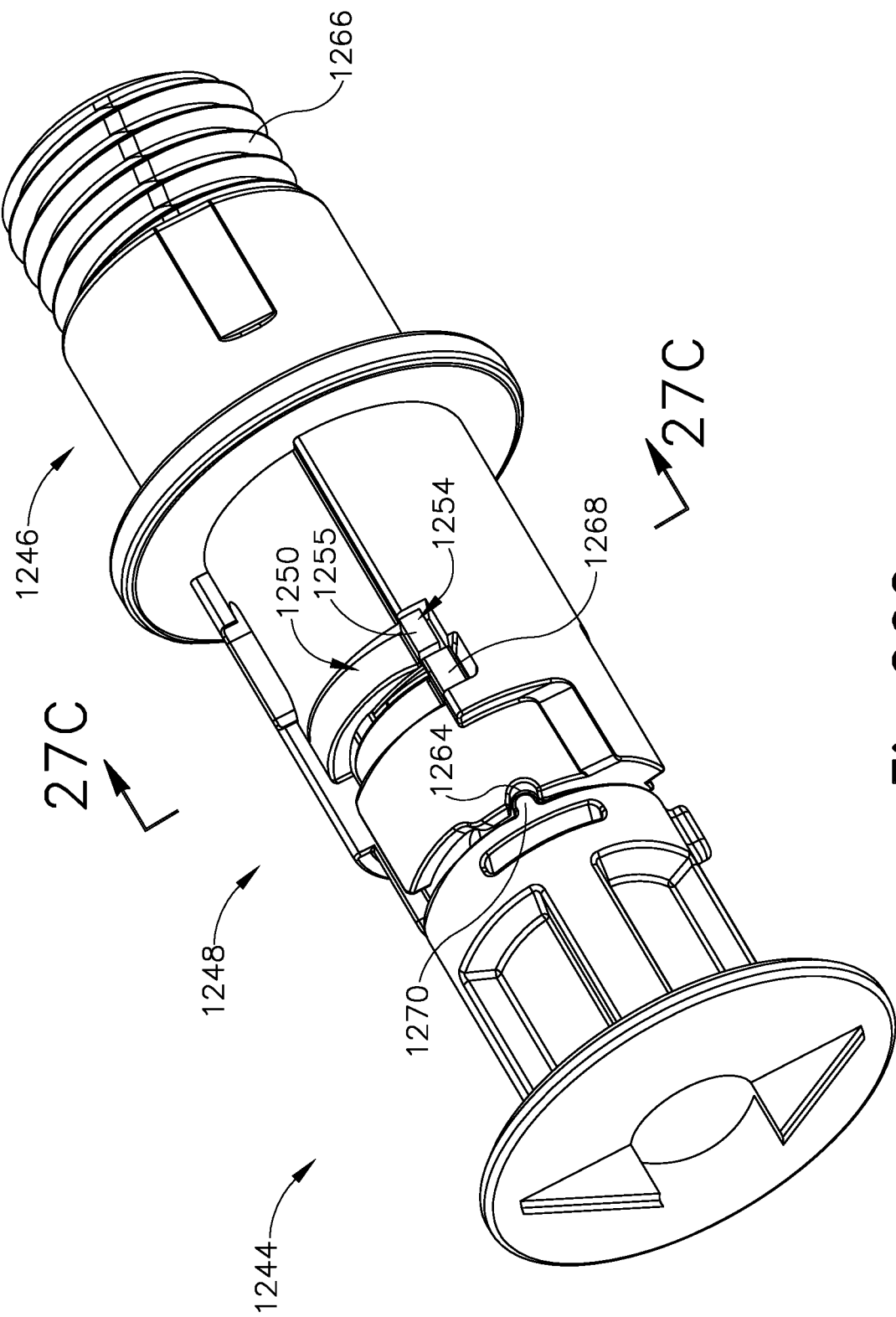
FIG. 26C depicts the schematic perspective view of the mechanical lockout assembly similar to FIG. 26B, but in the unlocked configuration.
Figure 27A:
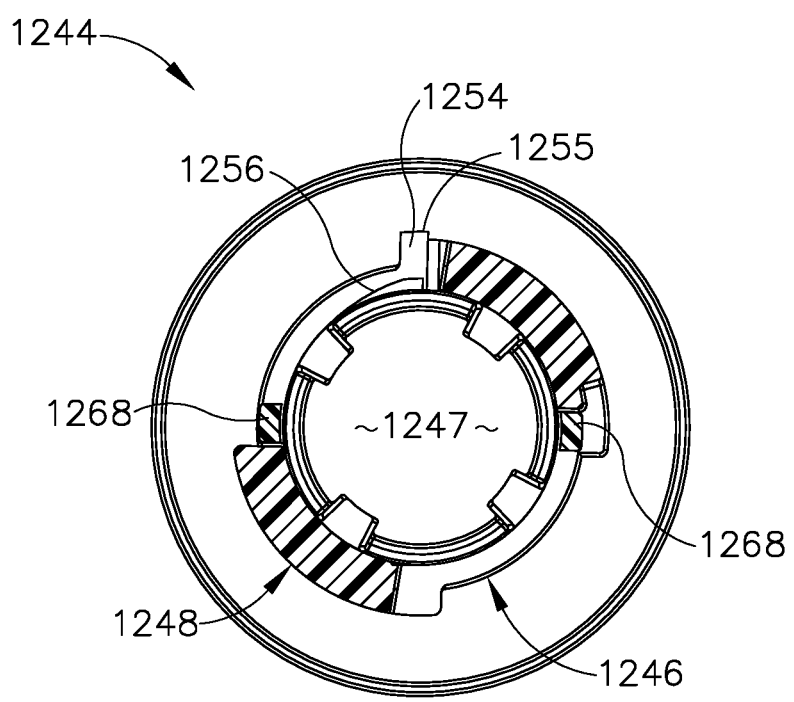
FIG. 27A depicts a schematic enlarged cross-sectional view of FIG. 26A taken along section line 27A-27A of FIG. 26A.
Figure 27B:
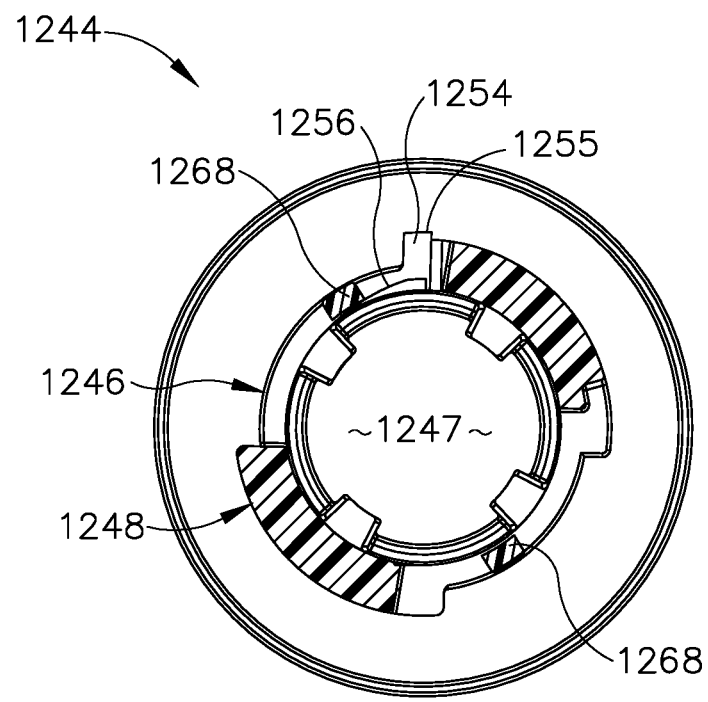
FIG. 27B depicts a schematic enlarged cross-sectional view of FIG. 26B taken along section line 27B-27B of FIG. 26B.
Figure 27C:
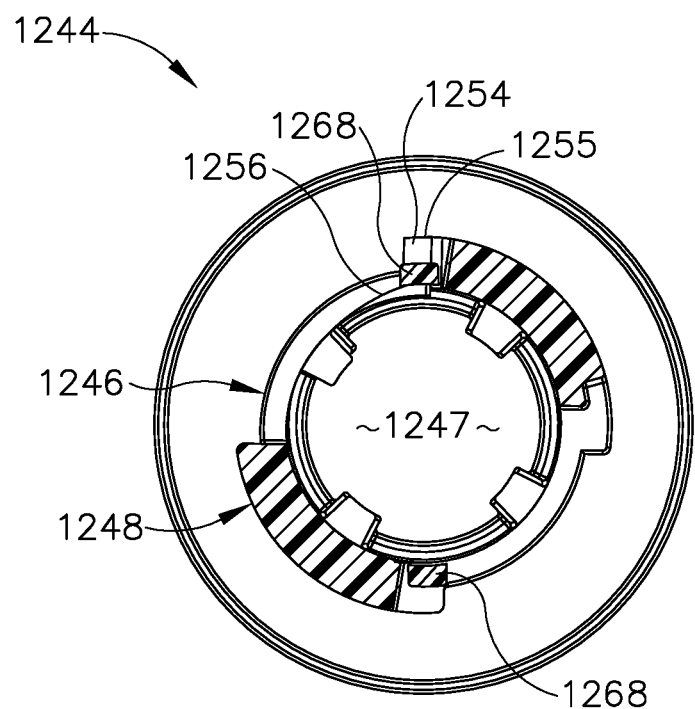
FIG. 27C depicts a schematic enlarged cross-sectional view of FIG. 26C taken along section line 27C-27C of FIG. 26C.

FIG. 25 shows bayonet collar (1248) as including at least one bayonet projection (1268), with two being shown in FIGS. 27A-27C, configured to contact cam surface (1256) of spring leg (1250) as bayonet collar (1248) is rotated relative to outer tube collar (1246) from a locked configuration to an unlocked configuration. Bayonet collar (1248) also includes protrusions (1270) that are configured to be received in cutouts (1264) as shown in FIG. 26C, to provide a detent coupling. Bayonet projection (1268) serves two purposes. First, bayonet projection (1268) pulls down interference tab (1254) to disengage interference tab (1254) from a lateral aperture (1276) in rotation collar (1249) shown in FIG. 28, thereby allowing the clamp arm drivetrain to translate longitudinally. Second, bayonet projection (1268) provides a coupling between bayonet collar (1248) and outer tube collar (1246), such that longitudinal motion of outer tube collar (1246) is communicated to bayonet collar (1248). When interference tab (1254) is disengaged from lateral aperture (1276) of rotation collar (1249) (see FIG. 28), movement of the clamp arm actuation assembly components within handle assembly (1212) is communicated to outer tube (1234) of shaft assembly (1214) via the engagement between outer tube and bayonet collars (1246, 1248), as provided by interference tab (1254).

Figure 26A:
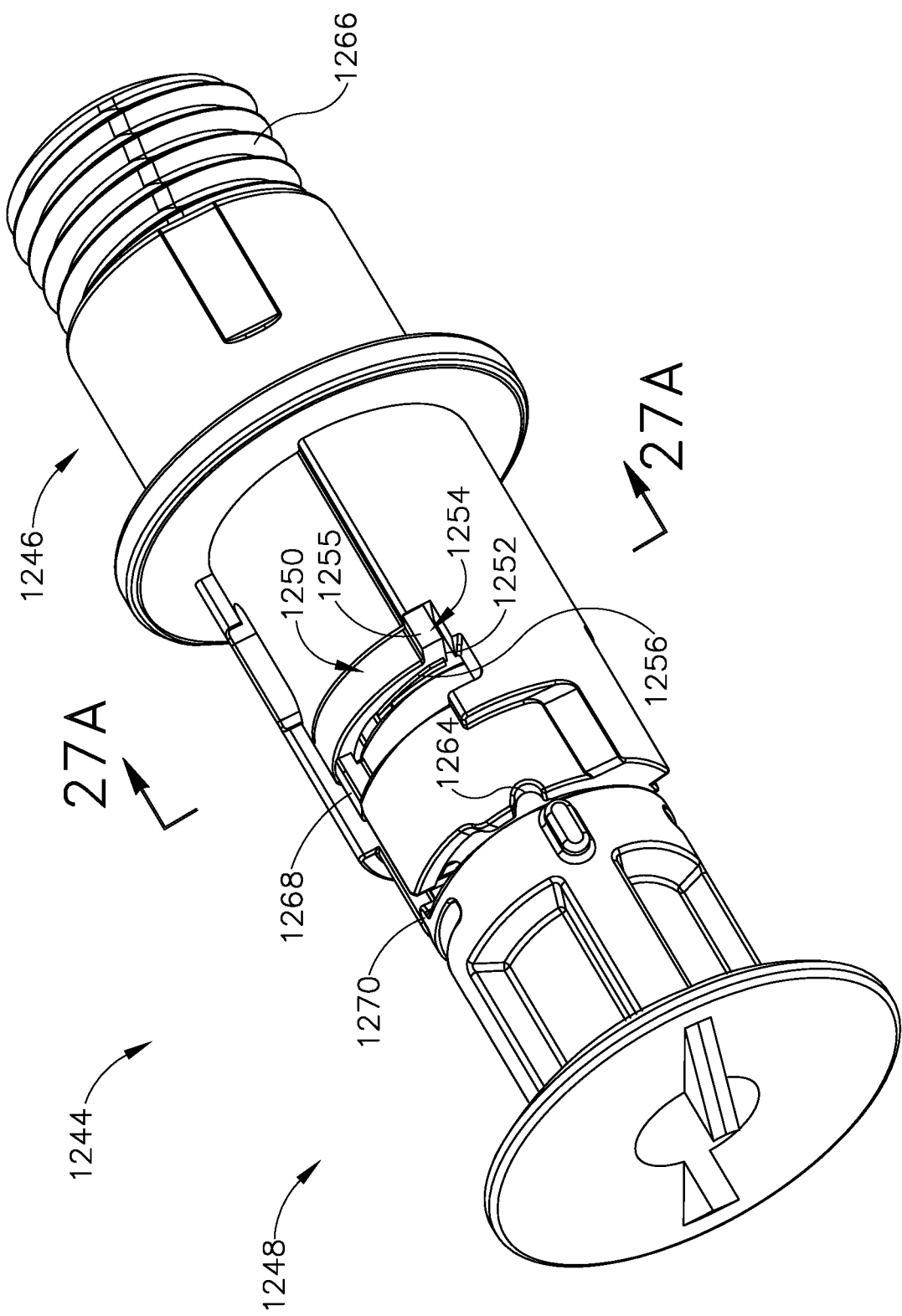
FIG. 26A depicts a schematic perspective view of the mechanical lockout assembly of FIG. 23 including the outer tube collar coupled with the bayonet collar in a locked configuration.
Figure 28:
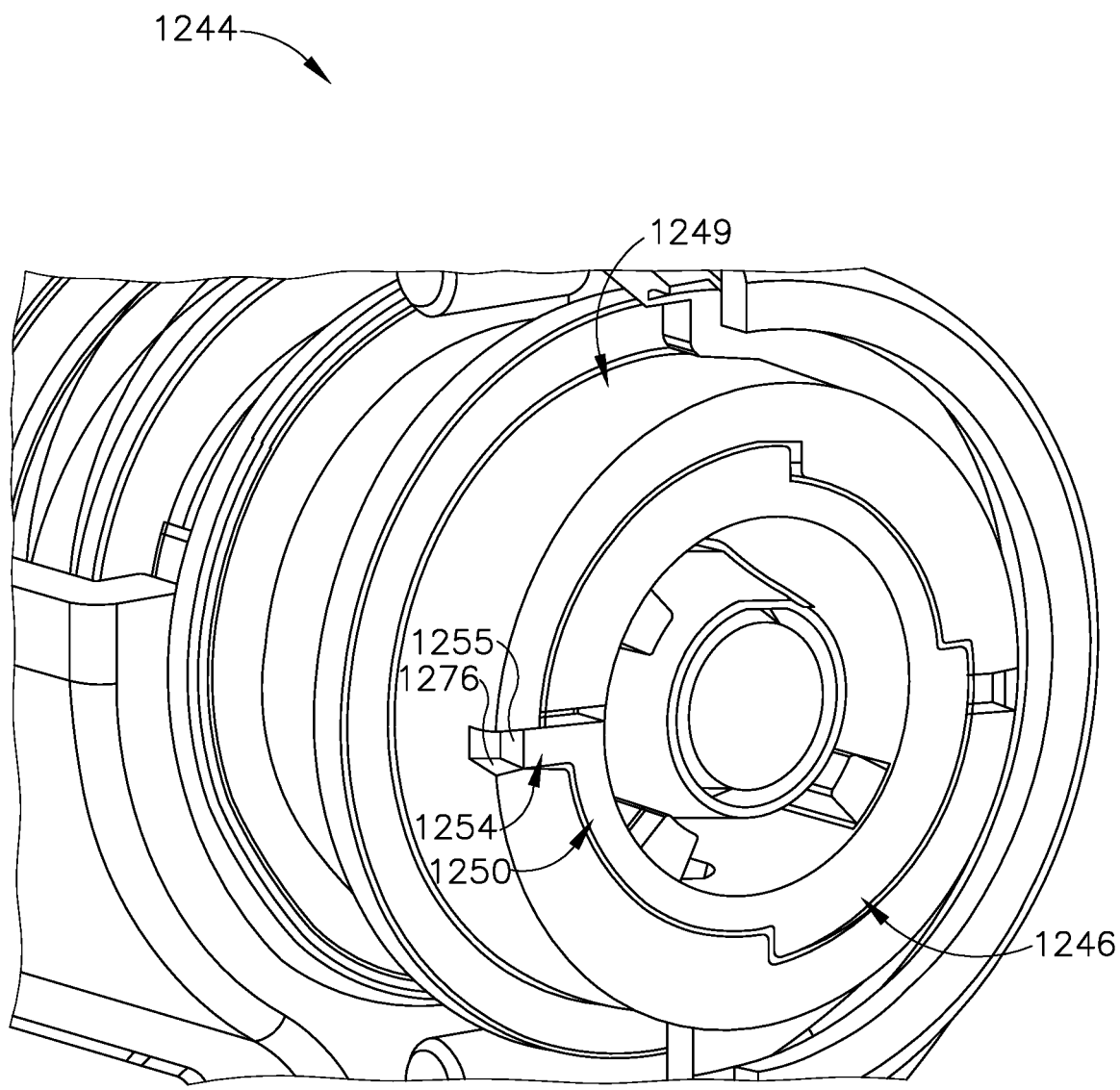
FIG. 28 depicts a schematic sectional view of the outer tube collar coupled with the rotation collar in the locked configuration.

FIGS. 26A, 27A, and 28 show instrument (1210) in the locked configuration, where handle assembly (1212) and shaft assembly (1214) are not fully coupled together. Rotation collar (1249) (see FIG. 28), includes a lateral aperture (1276) that receives interference tab (1254) to provide the locked configuration. In the locked configurations shown in FIGS. 26A, 27A, and 28, when interference tab (1254) of outer tube collar (1246) is positioned in lateral aperture (1276) of rotation collar (1249), outer tube collar (1246) is unable to translate. When outer tube collar (1246) is prevented from translating, trigger (1224) cannot be pivoted, and clamp arm (1230) cannot be pivoted toward ultrasonic blade (1228). At this stage, shaft assembly (1214) has been fully inserted longitudinally into handle assembly (1212), shown by bayonet collar (1248) contacting outer tube collar (1246). However, shaft assembly (1212) has not yet been rotated relative to handle assembly (1212) to fully seat shaft assembly (1214). More specifically, in the locked configuration, resilient interference tab (1254) of outer tube collar (1246) is not deflected inwardly, but instead is captured in lateral aperture (1276) of rotation collar (1249) shown in FIG. 28. As a result, mechanical lockout assembly (1244) prevents the operator from activating instrument (1210) using clamp arm closure trigger (1224). As shown in FIG. 27A, a central aperture (1247) extends through both outer tube collar (1246) and bayonet collar (1248) to receive an ultrasonic waveguide (not shown).

Figure 26B:
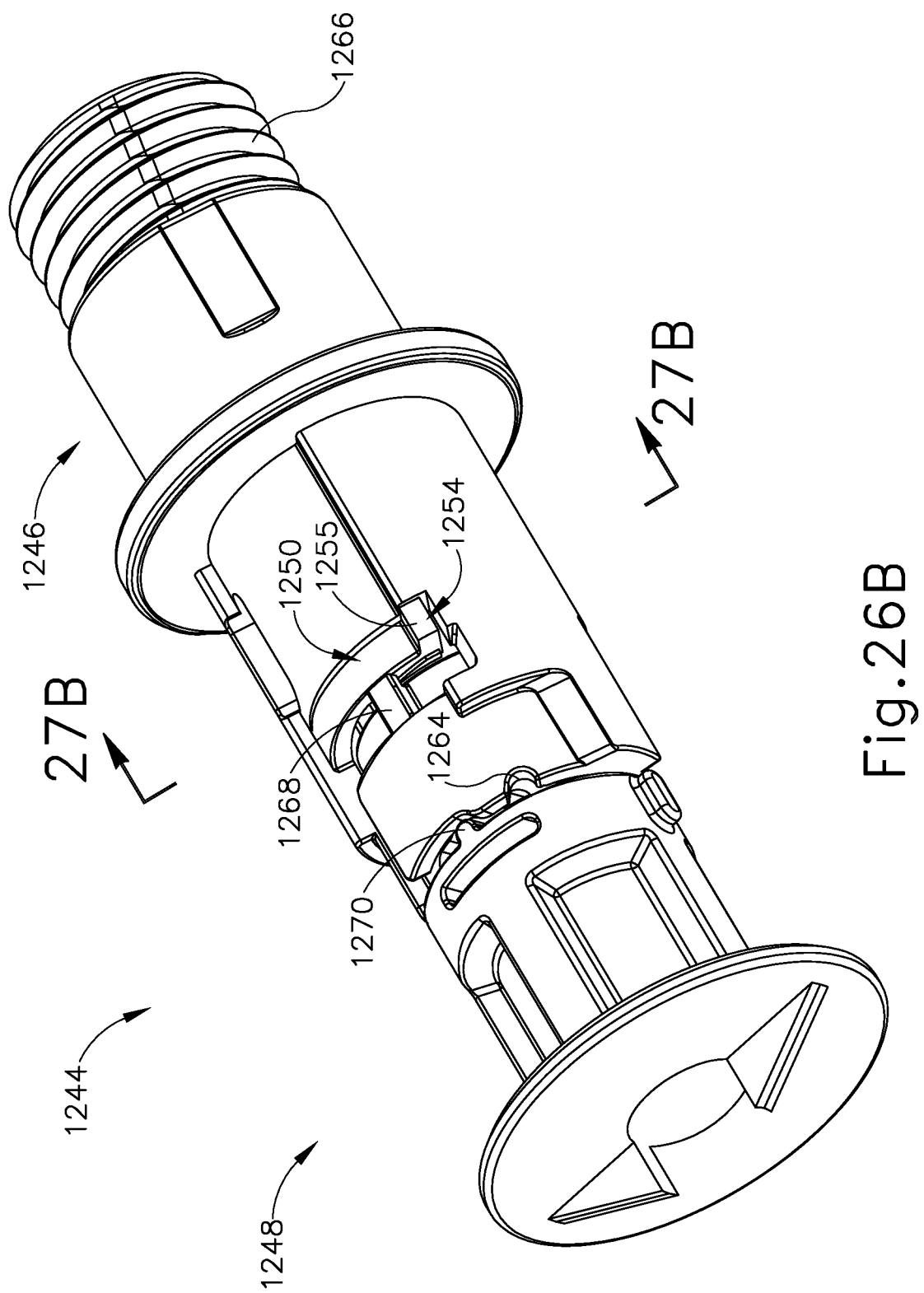
FIG. 26B depicts the schematic perspective view of the mechanical lockout assembly similar to FIG. 26A, moving from the locked configuration towards an unlocked configuration.

FIGS. 26B and 27B show instrument (1210) transitioning between the locked configuration and the unlocked configurations, with the operator still being prohibited from actuating trigger (1224). As shown, resilient interference tab (1254) is being pulled inward and outward of lateral aperture (1276) in rotation collar (1249) when bayonet collar (1248) is rotated. Bayonet projection (1268) rides along cam surface (1256) as bayonet collar (1248) is rotated, which pulls cam surface (1256) and the rest of resilient interference tab (1254) inward. As shown, cam surface (1256) is integrally formed as a unitary piece together with resilient interference tab (1254). More specifically, bayonet projection (1268) includes a radially extending component which travels through passageways (1258, 1262) and a proximally extending component which pulls down the spring leg (1250) supporting resilient interference tab (1254).

FIGS. 26C and 27C show instrument (1210) in the unlocked configuration, where handle assembly (1212) and shaft assembly (1214) are completely coupled together, such that the operator is able to activate instrument (1210) using trigger (1222). When interference tab (1254) is pulled out of lateral aperture (1276) of rotation collar (1249), outer tube collar (1246) is then free to translate, thereby enabling pivotal movement of trigger (1224), thereby enabling closure of clamp arm (1230) toward ultrasonic blade (1228). In the unlocked configuration, bayonet projections (1268) on bayonet collar (1248) push resilient interference tab (1254) inwards towards a center of outer tube collar (1246), enabling the shaft assembly (1214) including clamp arm (1230) to function. Outer tube (1234) translates relative to the rest of shaft assembly (1214) to provide pivotal movement of clamp arm (1230) toward/away from ultrasonic blade (1228). When the operator rotates shaft assembly (1214) to fully assemble instrument (1210), the operator would want to grasp rotation knob (1242) and hold it stationary.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) a handle assembly including at least one operator input feature; (b) an ultrasonic transducer supported by the handle assembly; (c) a shaft assembly configured to removably couple with the handle assembly, wherein the shaft assembly includes a distal end portion, wherein the shaft assembly further includes: (i) an end effector extending distally from the distal end portion, and (ii) an ultrasonic waveguide configured to be acoustically coupled with the ultrasonic transducer; and (d) a mechanical lockout assembly configured to move between at least an unlocked configuration and a locked configuration, wherein in the locked configuration, the handle assembly and the shaft assembly are only partially coupled together physically preventing the operator from activating the instrument using the operator input feature, and wherein in the unlocked configuration, the handle assembly and shaft assembly are completely coupled together enabling the operator to activate the instrument using the operator input feature.

Example 2

The ultrasonic surgical instrument of Example 1, wherein in the locked configuration, the mechanical lockout assembly prevents the operator input feature of activating a trigger of the handle assembly that is operatively coupled with the end effector, wherein preventing activation of the trigger prevents the operator from clamping on tissue with the end effector.

Example 3

The ultrasonic surgical instrument of any one or more of Examples 1 through 2, wherein in the locked configuration, the mechanical lockout assembly prevents the operator input feature of activating at least one energy control button disposed on the handle assembly preventing the operator from activating the ultrasonic blade.

Example 4

The ultrasonic surgical instrument of any one or more of Examples 1 through 3, wherein a spring pushes the mechanical lockout assembly from the locked configuration to the unlocked configuration when the shaft assembly is removed from the handle assembly.

Example 5

The ultrasonic surgical instrument of any one or more of Examples 1 through 4, wherein the operator input feature includes at least one energy control button separated by a passageway from a switch within the handle assembly, wherein the mechanical lockout assembly further includes a barrier that includes a body portion and at least one aperture that translates within the passageway between the locked configuration and the unlocked configuration, wherein in the locked configuration when the shaft assembly is not completely coupled with the handle assembly, the body portion is disposed within the passageway between the energy control button and the switch preventing the switch from activating the instrument, and wherein in the unlocked configuration when the shaft assembly is completely coupled with the handle assembly, the aperture is disposed within the passageway between the energy control button and the switch enabling the switch to activate the instrument.

Example 6

The ultrasonic surgical instrument of any one or more of Examples 1 through 5, wherein the barrier includes a flexible member that is operatively coupled with the shaft assembly, wherein the flexible element is pushed into the passageway such that in the locked configuration the flexible member extends between the energy control button and the switch.

Example 7

The ultrasonic surgical instrument of any one or more of Examples 1 through 6, wherein in the unlocked configuration, at least one of the energy control button or the switch extends at least partially through the aperture of the barrier and makes direct physical contact with the other of the energy control button or the switch through the aperture.

Example 8

The ultrasonic surgical instrument of any one or more of Examples 1 through 7, wherein the mechanical lockout assembly further includes an angled slide that is configured to be contacted by a projection of the shaft assembly, wherein the angled slide is configured to contact the barrier causing the mechanical lockout assembly to transition from the locked configuration to the unlocked configuration, and wherein in the locked configuration, the body portion of the barrier is disposed within the passageway between the energy control button and the switch preventing the switch from activating the instrument.

Example 9

The ultrasonic surgical instrument of any one or more of Examples 1 through 8, wherein the shaft assembly includes a projection that contacts the angled slide causing an angled proximal end of angled slide to push the barrier further into the passageway using a camming action.

Example 10

The ultrasonic surgical instrument of any one or more of Examples 1 through 9, wherein the handle assembly includes the operator input feature that includes at least one switch and a first portion of an energy control button, wherein the shaft assembly includes a second portion of an energy control button, wherein in the locked configuration when the shaft assembly is partially coupled with the handle assembly, misalignment of the first and second portions of the energy control button prevents the switch from activating the instrument, and wherein in the unlocked configuration when the shaft assembly is completely coupled with the handle assembly, alignment of the first and second portions of the energy control button enables the switch to activate the instrument.

Example 11

The ultrasonic surgical instrument of any one or more of Examples 1 through 10, wherein the handle assembly includes the operator input feature, wherein the operator input feature includes a trigger, wherein the mechanical lockout assembly further includes a closure lever link operatively coupled with the trigger, wherein in the locked configuration when the shaft assembly is partially coupled with the handle assembly, the closure lever link is pulled over center in a first direction, preventing the closure lever link from being rotated closed which prevents the trigger from being actuated which prevents the end effector from closing, and wherein in the unlocked configuration when the shaft assembly is completely coupled with the handle assembly, insertion of the shaft assembly causes the closure lever link to rotate in a second direction that is opposite the first direction allowing the trigger to be actuated enabling the end effector to close.

Example 12

The ultrasonic surgical instrument of any one or more of Examples 1 through 11, wherein the mechanical lockout assembly further includes a one-way door that is configured to be opened by coupling the shaft assembly with the handle assembly, wherein in the locked configuration when the shaft assembly is partially coupled with the handle assembly, the one-way door prevents a connecting portion of the ultrasonic transducer from reaching a connecting portion of a proximal end of the ultrasonic waveguide; wherein in moving from the locked configuration to the unlocked configuration, as an outer sheath is rotated, a translatable jacket threadably coupled with the outer sheath translates longitudinally relative to the one-way door pivoting the one-way door to an open position allowing the connecting portions of the ultrasonic transducer and the ultrasonic waveguide to acoustically couple, and wherein in the unlocked configuration when the shaft assembly is completely coupled with the handle assembly allowing end effector to be actuated using the operator input feature.

Example 13

The ultrasonic surgical instrument of any one or more of Examples 1 through 12, wherein a proximal portion of the shaft assembly includes a projection, wherein the mechanical lockout assembly includes a coupling device operatively coupled with the handle assembly, and wherein the coupling device includes a guide track that is configured to translate and rotate the shaft assembly using the interaction between the projection of the shaft assembly and the guide track of the coupling device from the locked configuration when the shaft assembly is partially coupled with the handle assembly to the unlocked configuration when the shaft assembly is completely coupled with the handle assembly.

Example 14

The ultrasonic surgical instrument of any one or more of Examples 1 through 13, wherein the coupling device translates longitudinally in response to pivotal movement of a trigger, and wherein the coupling device operatively couples the trigger with the clamp arm of the shaft assembly.

Example 15

The ultrasonic surgical instrument of any one or more of Examples 1 through 14, wherein the mechanical lockout assembly includes: (i) an outer tube collar coupled with the handle assembly, wherein the outer tube collar includes a spring leg that includes a distal end, wherein the distal end of the spring leg includes a resilient interference tab; and (ii) a bayonet collar coupled with the shaft assembly, wherein the bayonet collar includes a bayonet projection that is configured to contact a cam surface of the spring leg as the bayonet collar is rotated relative to the outer tube collar from the locked configuration to the unlocked configuration; and (iii) a rotation collar that includes an aperture, wherein in the locked configuration when the shaft assembly is partially coupled with the handle assembly, the interference tab of the outer tube collar deflects outwardly into the aperture of the rotation collar preventing activation of the instrument, and wherein in the unlocked configuration when the shaft assembly is completely coupled with the handle assembly, the bayonet projection contacts the cam surface of the interference tab to deflect the interference tab inwardly, enabling activation of the instrument.

Example 16

The ultrasonic surgical instrument of any one or more of Examples 1 through 15, wherein a spring pushes the body portion of the barrier from the locked configuration to the unlocked configuration when the shaft assembly is removed from the handle assembly.

Example 17

An ultrasonic surgical instrument, comprising: (a) a handle assembly including at least one energy control button that is separated by a passageway from a switch within the handle assembly; (b) an ultrasonic transducer supported by the handle assembly; (c) a shaft assembly configured to removably couple with the handle assembly, wherein the shaft assembly includes a distal end portion, wherein the shaft assembly further includes: (i) an end effector extending distally from the distal end portion, and (ii) an ultrasonic waveguide configured to be acoustically coupled with the ultrasonic transducer; and (d) a barrier that includes a body portion and at least one aperture extending at least partially through the body portion, wherein the barrier translates within the passageway between the locked configuration and the unlocked configuration, wherein in the locked configuration, the body portion is disposed within the passageway between the energy control button and the switch preventing the switch from activating the instrument, and wherein in the unlocked configuration, the aperture is disposed within the passageway between the energy control button and the switch, and at least one of the energy control button or the switch extends at least partially through the aperture of the barrier and makes direct physical contact with the other of the energy control button or the switch through the aperture enabling the switch to activate the instrument.

Example 18

A method of operating an ultrasonic surgical instrument, wherein the ultrasonic surgical instrument comprises: (a) a handle assembly including at least one operator input feature and an ultrasonic transducer supported by the handle assembly; (b) a shaft assembly configured to removably couple with the handle assembly, wherein the shaft assembly includes a distal end portion, wherein the shaft assembly further includes: (i) an end effector extending distally from the distal end portion, and (ii) an ultrasonic waveguide configured to be acoustically coupled with the ultrasonic transducer; and (c) a mechanical lockout assembly configured to move between at least an unlocked configuration and a locked configuration, wherein the method comprises: (a) inhibiting the operator input feature from activating the instrument while in the locked configuration when the handle assembly and the shaft assembly are partially coupled together, wherein inhibiting activation of the instrument provides instant feedback to an operator; (b) coupling the handle assembly and the shaft assembly completely together to disarm the locking assembly; and (c) activating the instrument using the operator input feature when in the unlocked configuration.

Example 19

The method of Example 18, wherein the inhibiting activation further includes the mechanical lockout assembly preventing the operator input feature of locking an operator activated trigger of the handle assembly that is operatively coupled with the end effector, thereby preventing the operator from clamping on tissue with the end effector.

Example 20

The method of any one or more of Examples 18 through 19, wherein the inhibiting activation further includes the mechanical lockout assembly preventing the operator input feature of activating at least one energy control button preventing the operator from activating the ultrasonic blade.

IV. MISCELLANEOUS

It should be understood that the various teachings herein may be readily combined with the various teachings of U.S. Pub. No. 2017/0105754, entitled "Surgical Instrument with Dual Mode End Effector and Side-Loaded Clamp Arm Assembly," published on April 2017, the disclosure of which is incorporated by reference herein. Various suitable ways in which the teachings herein may be combined with the teachings of U.S. Pub. No. 2017/0105754 will be apparent to those of ordinary skill in the art.

It should be understood that the various teachings herein may be readily combined with the various teachings of U.S. Pub. No. 2017/0105755, entitled "Surgical Instrument with Dual Mode End Effector and Compound Lever with Detents," published on Apr. 20, 2017, the disclosure of which is incorporated by reference herein. Various suitable ways in which the teachings herein may be combined with the teachings of U.S. Pub. No. 2017/0105755 will be apparent to those of ordinary skill in the art.

It should be understood that the various teachings herein may be readily combined with the various teachings of U.S. Pub. No. 2017/0105788, entitled "Surgical Instrument with Dual Mode End Effector and Modular Clamp Arm Assembly," filed on Apr. 20, 2017, issued as U.S. Pat. No. 10,893,914 on Jan. 19, 2021, the disclosure of which is incorporated by reference herein. Various suitable ways in which the teachings herein may be combined with the teachings of U.S. Pub. No. 2017/0105788, issued as U.S. Pat. No. 10,893,914 on Jan. 19, 2021 will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) a handle assembly including at least one user input feature configured to selectively mechanically actuate from a first position to a second position to thereby activate the instrument in the second position;
   (b) an ultrasonic transducer supported by the handle assembly, wherein the ultrasonic transducer is operatively connected to the at least one user input feature;
   (c) a shaft assembly configured to removably couple with the handle assembly, wherein the shaft assembly includes a distal end portion, wherein the shaft assembly further includes:
      (i) an end effector extending distally from the distal end portion, and
      (ii) an ultrasonic waveguide configured to be acoustically coupled with the ultrasonic transducer; and
   (d) a mechanical lockout assembly configured to move between at least an unlocked configuration and a locked configuration,
   wherein in the locked configuration the mechanical lockout assembly prevents selective mechanical actuation of the at least one user input feature from the first position to the second position such that the handle assembly and the shaft assembly are only partially coupled together physically preventing the user from activating the instrument using the at least one user input feature, and
   wherein in the unlocked configuration the mechanical lockout assembly allows selective mechanical actuation of the at least one user input feature from the first position to the second position such that the handle assembly and the shaft assembly are completely coupled together enabling the user to activate the instrument using the at least one user input feature.

2. The ultrasonic surgical instrument of claim 1, wherein in the locked configuration, the mechanical lockout assembly prevents the at least one user input feature from activating at least one switch disposed in the handle assembly thereby preventing the user from activating the ultrasonic transducer.

3. The ultrasonic surgical instrument of claim 1, wherein a spring pushes the mechanical lockout assembly to the locked configuration from the unlocked configuration when the shaft assembly is removed from the handle assembly.

4. The ultrasonic surgical instrument of claim 1, wherein the at least one user input feature includes at least one energy control button separated by a passageway from a switch within the handle assembly, wherein the mechanical lockout assembly further includes a barrier that includes a body portion and at least one aperture that translates within the passageway between the locked configuration and the unlocked configuration, wherein in the locked configuration when the shaft assembly is not completely coupled with the handle assembly, the body portion is disposed within the passageway between the at least one energy control button and the switch preventing the switch from activating the instrument, and wherein in the unlocked configuration when the shaft assembly is completely coupled with the handle assembly, the at least one aperture is disposed within the passageway between the at least one energy control button and the switch enabling the switch to activate the instrument.

5. The ultrasonic surgical instrument of claim 4, wherein the barrier includes a flexible member that is operatively coupled with the shaft assembly, wherein the flexible member is pushed into the passageway such that in the locked configuration the flexible member extends between the at least one energy control button and the switch.

6. The ultrasonic surgical instrument of claim 4, wherein in the unlocked configuration, at least one of the at least one energy control button or the switch extends at least partially through the at least one aperture of the barrier and makes direct physical contact with the other of the at least one energy control button or the switch through the at least one aperture.

7. The ultrasonic surgical instrument of claim 4, wherein the mechanical lockout assembly further includes an angled slide that is configured to be contacted by a projection of the shaft assembly, wherein the angled slide is configured to contact the barrier causing the mechanical lockout assembly to transition from the locked configuration to the unlocked configuration, and wherein in the locked configuration, the body portion of the barrier is disposed within the passageway between the at least one energy control button and the switch preventing the switch from activating the instrument.

8. An ultrasonic surgical instrument, comprising:
(a) a handle assembly including an energy control button that is separated by a passageway from a switch within the handle assembly;
(b) an ultrasonic transducer supported by the handle assembly;
(c) a shaft assembly configured to removably couple with the handle assembly, wherein the shaft assembly includes a distal end portion, wherein the shaft assembly further includes:
(i) an end effector extending distally from the distal end portion, and
(ii) an ultrasonic waveguide configured to be acoustically coupled with the ultrasonic transducer; and
(d) a barrier that includes a body portion and at least one aperture extending at least partially through the body portion, wherein the barrier translates within the passageway between a locked configuration and an unlocked configuration,
wherein in the locked configuration, the body portion is disposed within the passageway between the energy control button and the switch preventing the switch from activating the instrument, and
wherein in the unlocked configuration, the at least one aperture is disposed within the passageway between the energy control button and the switch, and at least one of the energy control button or the switch extends at least partially through the at least one aperture of the barrier and makes direct physical contact with the other of the energy control button or the switch through the at least one aperture enabling the switch to activate the instrument.

9. The ultrasonic surgical instrument of claim 8, wherein a spring pushes the body portion of the barrier to the locked configuration from the unlocked configuration when the shaft assembly is removed from the handle assembly.

10. An ultrasonic surgical instrument, comprising:
(a) a handle assembly including a user input feature and a switch, wherein the switch is configured to be selectively actuated by the user input feature;
(b) an ultrasonic transducer supported by the handle assembly and operatively connected to the switch such that the switch is configured to activate the ultrasonic transducer;
(c) a shaft assembly configured to removably couple with the handle assembly, wherein the shaft assembly includes a distal end portion, wherein the shaft assembly further includes:
(i) an end effector extending distally from the distal end portion, and
(ii) an ultrasonic waveguide configured to be acoustically coupled with the ultrasonic transducer; and
(d) a mechanical lockout assembly including a barrier configured to move between at least an unlocked configuration and a locked configuration,
wherein in the locked configuration, the barrier is disposed in a first position to block movement of the user input feature thereby preventing the switch from activating the ultrasonic transducer, and
wherein in the unlocked configuration, the barrier is in a second position to enable movement of the user input feature thereby enabling the switch to activate the ultrasonic transducer.

11. The ultrasonic surgical instrument of claim 10, wherein in the locked configuration, the handle assembly and the shaft assembly are only partially coupled together physically preventing the user from activating the ultrasonic transducer using the user input feature, and wherein in the unlocked configuration, the handle assembly and the shaft assembly are completely coupled together enabling the user to activate the ultrasonic transducer using the user input feature.

12. The ultrasonic surgical instrument of claim 11, wherein the handle assembly further includes a passageway between the user input feature and the switch, wherein the barrier is positioned within the passageway and configured to move within the passageway from the first position to the second position.

13. The ultrasonic surgical instrument of claim 12, wherein the barrier is configured to translate from the first position to the second position.

14. The ultrasonic surgical instrument of claim 13, wherein the barrier includes a body portion and an aperture, wherein the body portion of the barrier in the first position of the locked configuration is between the user input feature and the switch thereby blocking movement of the user input feature, wherein the aperture of the barrier in the second position of the unlocked configuration is between the user input feature and the switch thereby enabling movement of the user input feature.

15. The ultrasonic surgical instrument of claim 14, wherein the user input feature includes an energy control button operatively connected to the ultrasonic transducer.

* * * * *